US009232996B2

(12) United States Patent
Sun et al.

(10) Patent No.: US 9,232,996 B2
(45) Date of Patent: Jan. 12, 2016

(54) PROSTHETIC HEART VALVE

(75) Inventors: Wei Sun, South Windsor, CT (US); Eric Sirois, Plainfield, CT (US); Thuy Minh Pham, Hartford, CT (US); Kewei Li, Coventry, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 49 days.

(21) Appl. No.: 14/001,162

(22) PCT Filed: Feb. 24, 2012

(86) PCT No.: PCT/US2012/026440
§ 371 (c)(1),
(2), (4) Date: Feb. 3, 2014

(87) PCT Pub. No.: WO2012/161786
PCT Pub. Date: Nov. 29, 2012

(65) Prior Publication Data
US 2014/0155995 A1 Jun. 5, 2014

Related U.S. Application Data

(60) Provisional application No. 61/463,958, filed on Feb. 25, 2011.

(51) Int. Cl.
*A61F 2/24* (2006.01)
(52) U.S. Cl.
CPC ............. *A61F 2/2418* (2013.01); *A61F 2/2412* (2013.01); *A61F 2/2457* (2013.01)
(58) Field of Classification Search
USPC ................................. 623/2.18, 2.11
See application file for complete search history.

(56) References Cited

U.S. PATENT DOCUMENTS

| 7,455,689 | B2 | 11/2008 | Johnson | 623/2.14 |
| 2005/0075727 | A1 | 4/2005 | Wheatley | 623/20 |
| 2006/0195183 | A1 | 8/2006 | Navia | 623/2.18 |
| 2006/0276813 | A1 | 12/2006 | Greenberg | 623/1.24 |
| 2007/0282436 | A1* | 12/2007 | Pinchuk | 623/2.11 |

(Continued)

FOREIGN PATENT DOCUMENTS

| CN | 103687574 | 3/2014 |
| EP | 2677965 | 1/2014 |
| IN | 7651/DELNP/2013 | 11/2012 |

(Continued)

OTHER PUBLICATIONS

Sun W, et al. (2005) Simulated bioprosthetic heart valve deformation under quasi-static loading. J Biomech Eng. 127(6):905-914.

(Continued)

*Primary Examiner* — Yashita Sharma
*Assistant Examiner* — Tiffany Shipmon
(74) *Attorney, Agent, or Firm* — Ballard Spahr LLP

(57) ABSTRACT

A prosthetic heart valve having a stent, a plurality of leaflets positioned within the stent, and a suspension assembly coupled to the leaflets and the stent. The suspension assembly includes a central support structure that is spaced from the plurality of leaflets in the direction of blood flow. A plurality of elongate suspension members are secured to the central support structure, and at least one elongate suspension member is secured to each leaflet of the valve, thereby providing mechanical reinforcement for the leaflets.

101 Claims, 22 Drawing Sheets

(56) References Cited

U.S. PATENT DOCUMENTS

2008/0147183 A1   6/2008   Styrc .................... 623/2.12
2009/0276040 A1*  11/2009  Rowe et al. ............ 623/2.18

FOREIGN PATENT DOCUMENTS

WO          2007/024755 A1    3/2007
WO      WO 2012/161786        11/2012

OTHER PUBLICATIONS

Li K, et al. (2010) Simulated thin pericardial bioprosthetic valve leaflet deformation under static pressure-only loading conditions: implications for percutaneous valves. Ann Biomed Eng. 38(8):2690-2701.

Sun W, et al. (2010) Simulated elliptical bioprosthetic valve deformation: implications for asymmetric transcatheter valve deployment. J Biomech. 43(16):3085-3090.

Grube E, et al. (2007) Percutaneous aortic valve replacement for severe aortic stenosis in high-risk patients using the second-and current third-generation self-expanding CoreValve prosthesis: device success and 30-day clinical outcome. J Am Coll Cardiol. 50(1):69-67.

Webb JG, et al. (2007) Percutaneous transarterial aortic valve replacement in selected high-risk patients with aortic stenosis. Circulation. 116(7):755-763.

Zegdi R, et al. (2010) Increased radial force improves stent deployment in tricuspid but not in bicuspid stenotic native aortic valves. Ann Thorac Surg. 89(3):768-772.

Zegdi R, et al. (2008) Is it reasonable to treat all calcified stenotic aortic valves with a valved stent? Results from a human anatomic study in adults. J Am Coll Cardiol. 51(5):579-584.

Schultz CJ, et al. (2009) Geometry and degree of apposition of the CoreValve ReValving system with multislice computed tomography after implantation in patients with aortic stenosis. J Am Coll Cardiol. 54(10):911-918.

Thubrikar M, et al. (1981) the design of the normal aortic valve. Am J Physiol. 241(6):H795-801.

International Preliminary Report on Patentability issued Aug. 27, 2013 for PCT/US2012/026440 filed Feb. 24, 2012 and published as WO 2012/161786 on Nov. 29, 2012 (Inventors—Sun et al. // Applicant—University of Connecticut) (8 pages).

International Search Report & Written Opinion issued Jun. 28, 2013 for PCT/US2012/026440 filed Feb. 24, 2012 and published as WO 2012/161786 on Nov. 29, 2012 (Inventors—Sun et al. // Applicant—University of Connecticut) (18 pages).

Response to Communication Pursuant to Rules 161(2) and 162 EPC filed Mar. 12, 2014 for EP Application No. 12 789 673.6, which claims priority to PCT/US2012/026440 filed Feb. 24, 2012 (Inventors—Sun et al. // Applicant—University of Connecticut) (10 pages).

* cited by examiner

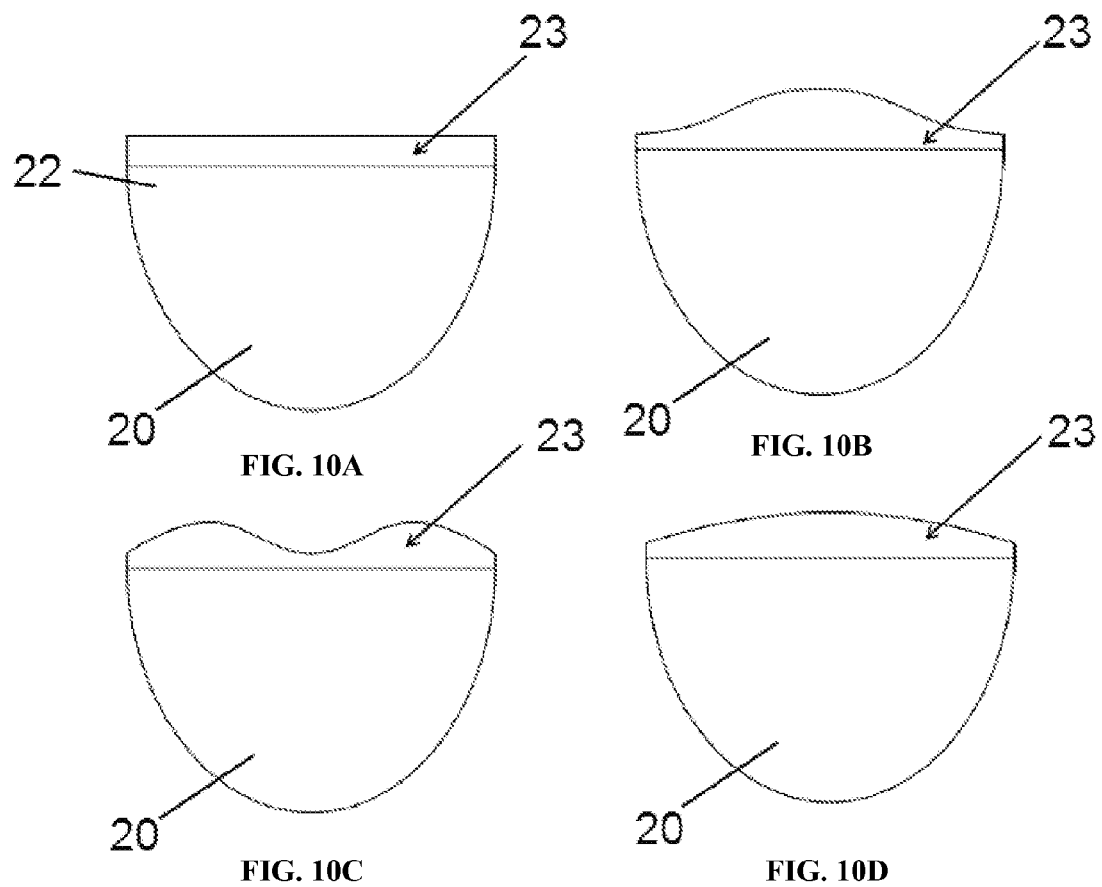

PROSTHETIC HEART VALVE

CROSS-REFERENCE TO RELATED APPLICATIONS

This application is a National Phase Application of International Application No. PCT/US2012/026440, filed Feb. 24, 2012, which claims priority to United States Patent Application No. 61/463,958, filed Feb. 25, 2011, which applications are incorporated herein fully by this reference.

FIELD

The invention relates to methods and devices for the treatment of valvular heart disease, and, more specifically, to prosthetic devices for use in minimally invasive, trans-catheter and surgical replacement of heart valves in subjects with aortic, mitral, pulmonary, and tricuspid valve diseases.

BACKGROUND

The human heart contains four valves: the tricuspid valve, the pulmonic valve, the mitral valve and the aortic valve. Proper functioning of each of these valves is essential to good health. A variety of pathologies, such as congenital defects, endocarditis, and rheumatic fever, can lead to dysfunction of one or more heart valves and, ultimately, to heart failure. Recent statistics show that each year, in the United States alone, valvular heart disease is responsible for nearly 20,000 deaths and is a contributing factor in approximately 42,000 deaths.

Surgical replacement of a diseased human heart valve with a prosthetic valve was first performed successfully in 1960. The procedure is now common, with approximately 300,000 patients worldwide undergoing heart valve replacement surgery each year. For the vast majority of patients, open heart surgical valve procedures provide an established form of therapy with reasonable risk and are proven to have long-term benefits.

The first practical experiment utilizing a minimally invasive, transcatheter heart valve (THV) was reported in 1992. Investigators fabricated a stent-mounted bioprosthetic valve and implanted it via balloon catheter, which demonstrated the feasibility of percutaneous implantation. The use of a stent-mounted bioprosthesis for pulmonic valve replacement was pioneered in 2000. Using a bovine jugular vein valve mounted within a stent, the first in-human percutaneous implantations of artificial valves in children with right ventricle to pulmonary prosthetic conduits were performed. This achievement clearly marked the beginning of the era of percutaneous valve replacement therapy in patients. The first in-human percutaneous aortic valve replacement was reported in 2002 on a 57-year-old man with inoperable critical aortic stenosis. Recently, in November 2011, U.S. FDA approved the Edwards SAPIEN transcatheter valve for use in the U.S. market.

Currently, transcatheter valve replacement holds promise for a large number of patients who otherwise have limited or no treatment options. However, it also poses various challenges due to its unique disease treatment mechanism. The transcatheter valve technique relies at least partially upon a frictional type of engagement between an expanded stent structure and the native tissue to maintain the position of the transcatheter valve for its normal function. The transcatheter valve stent can become partially embedded in the valve tissue during radial expansion. Improper host-implant interactions can lead to various dangerous events for the patient. For instance, excessive radial force from transcatheter aortic valve stent expansion may cause injury to the aorta, while insufficient force may lead to paravalvular leakage and device migration.

For patients with valve stenosis, heavy calcium deposition on the valve leaflets and on the valve root can also cause a distortion of transcatheter valve geometries, resulting in a valve of an elliptical shape instead of a nominal circular shape. Recent studies indicate that transcatheter aortic valve frames often do not reach their nominal designed dimensions but instead undergo asymmetric or non-circular expansion. An elliptical transcatheter valve configuration can result in negative clinical consequences, such as affecting leaflet coaptation, which can cause valve regurgitation. Furthermore, without proper leaflet apposition, uneven distribution of stress on the leaflets may affect a valve's long-term performance and durability.

Currently, transcatheter aortic valve replacement is not recommended for bicuspid aortic valve (BAV) patients because of the elliptical shape of the BAV and a high possibility of paravalvular leak caused by the gap between a circular transcatheter valve and an elliptical BAV shape. Recently, it has been found that a distorted, elliptical transcatheter aortic valve induces a significant increase in the leaflet peak stresses (143% at the eccentricity of 0.68) and strains (59% at the eccentricity of 0.68) compared with the nominal circular TAV under the same boundary/loading conditions.

An artificial heart valve that employs a leaflet design, whether a transcatheter heart valve or a surgical bioprosthetic heart valve, is susceptible to wear and tear of the leaflet material, due to normal valve cycling over prolonged periods of time. Studies have shown that the regions of tearing of bioprosthetic heart valve correlate with the regions of high tensile and bending stresses acting on the leaflets during opening and closing. Stress concentrations within the cusp can either directly accelerate tissue structural fatigue damage, or initiate calcification by causing structural disintegration, enabling multiple pathways of calcification that can lead to valve failure.

Thus, what is needed in the art is a prosthetic valve device that reduces leaflet stress and accommodates elliptical deformation of the transcatheter valve after implantation.

SUMMARY

Described herein is a prosthetic heart valve for implantation into a selected channel within the heart of a subject. The prosthetic heart valve includes a stent having an inner surface that defines an interior region of the stent. The prosthetic heart valve also includes a plurality of leaflets positioned within the interior region of the stent. Each leaflet defines a free edge, an attachment edge, and a pair of spaced commissure regions. The attachment edge of each leaflet is attached to the stent such that each commissure region of each respective leaflet is positioned proximate a commissure region of an adjacent leaflet. The prosthetic heart valve further includes a suspension assembly that mechanically reinforces the plurality of leaflets. The suspension assembly includes a central support structure that is coupled to the stent such that the central support structure is spaced from the plurality of leaflets in the direction of blood flow. The suspension assembly also includes a plurality of elongate suspension members that are secured to the central support structure. At least one suspension member of the plurality of suspension members is secured to each leaflet.

BRIEF DESCRIPTION OF THE FIGURES

These and other features of the disclosure will become more apparent in the detailed description in which reference is made to the appended drawings wherein:

FIGS. 10A-10D are two-dimensional flat form depictions of exemplary valve leaflets having extended edge portions as described herein.

FIGS. 11A and 11C show exemplary suspension members that are substantially perpendicularly oriented and/or branched relative to the free edge of the leaflet to which they are attached. FIGS. 11B and 11D show exemplary suspension members that are angularly oriented and/or branched relative to the free edge of the leaflet to which they are attached.

DETAILED DESCRIPTION

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a suspension member" can include two or more such suspension members unless the context indicates otherwise.

As used herein, the terms "optional" or "optionally" mean that the subsequently described event or circumstance may or may not occur, and that the description includes instances where said event or circumstance occurs and instances where it does not.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject can be used interchangeably with the term "patient."

As used herein, the term "commissure" generally refers to regions of adjacent leaflets of a prosthetic heart valve that are in proximity to and/or in contact with one another when the leaflets are secured in an operative position within a selected chamber of the heart of a subject.

Figure 1A:
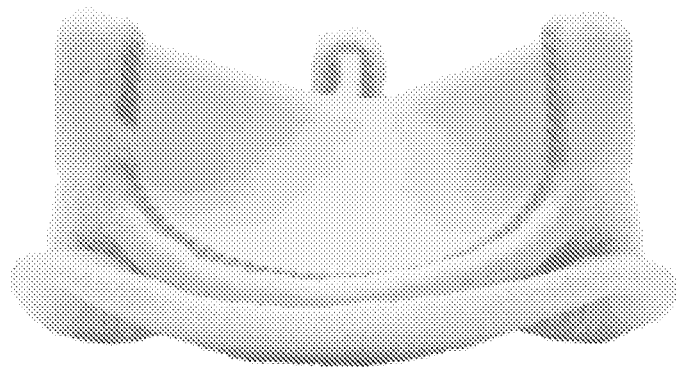
FIG. 1A is a perspective view of a prior art surgical heart valve assembly, showing three leaflets circumferentially attached to the valve.
Figure 1B:
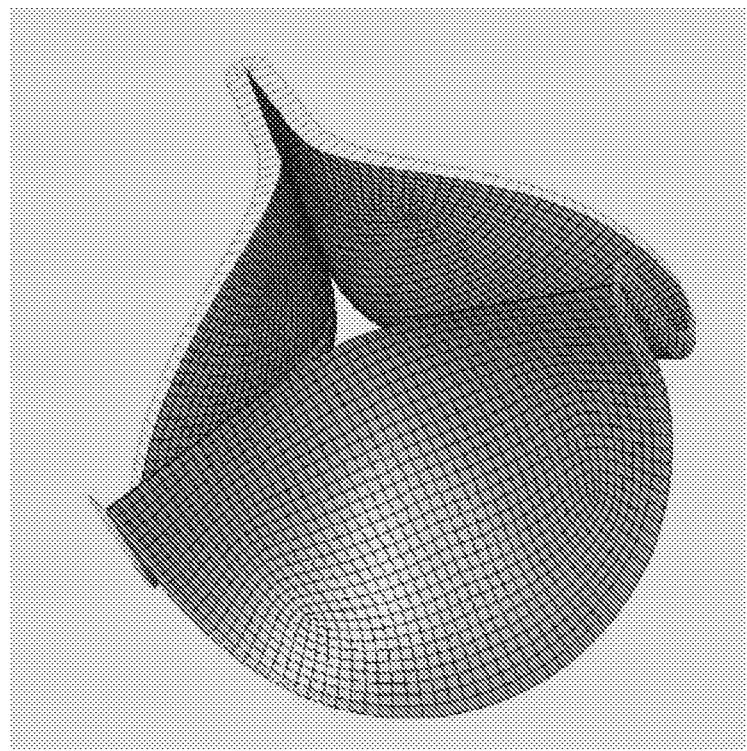
FIG. 1B is a perspective view of a computational model of a prior art tri-leaflet surgical heart valve assembly, showing three leaflets circumferentially attached to a valve wireform.
Figure 2:
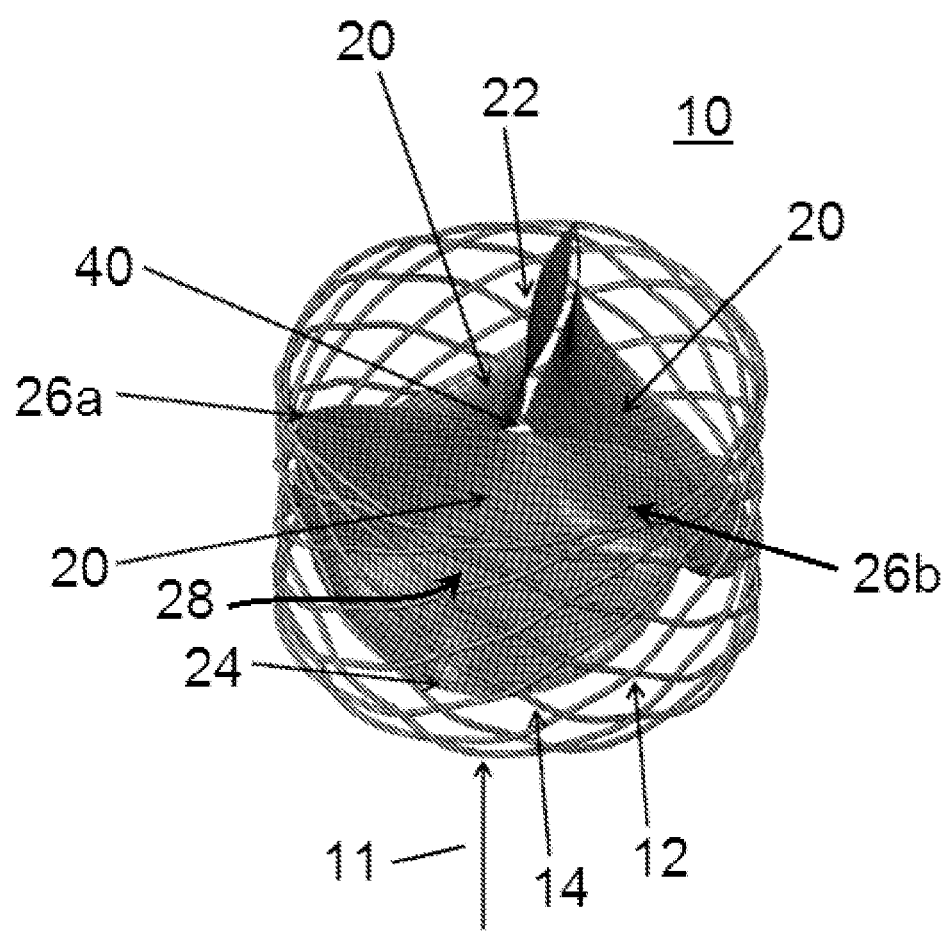
FIG. 2 is a perspective view of an exemplary prosthetic heart valve as described herein, showing three leaflets circumferentially attached to an expandable support stent.

In one embodiment, and with reference to FIGS. 1-18, the invention provides a prosthetic heart valve 10 for implantation into a selected channel within the heart of a subject. Within the selected channel, blood flows in a flow direction 11. With reference to FIG. 2, line 11 also corresponds to a flow axis. It is contemplated that the prosthetic heart valve disclosed herein can reduce valvular stresses and demonstrate improved long-term performance and durability compared to currently known prosthetic transcatheter valves, such as shown in FIGS. 1A-1B. In exemplary aspects, the selected channel within the heart of the subject can be the aorta. However, it is contemplated that the selected channel within the heart of the subject can be any channel within the heart, including, for example and without limitation, the mitral valve (bicuspid valve), the right ventricular valve (tricuspid valve), the pulmonary valve, and the like.

In one aspect, as shown in FIG. 2, the prosthetic heart valve 10 can comprise a stent 12 having an inner surface that defines an interior region 14 of the stent. Optionally, in another aspect, the stent 12 can be collapsible. Alternatively, it is contemplated that the stent 12 can be non-collapsible. In an additional aspect, the stent 12 can be expandable. In this aspect, it is contemplated that the stent 12 can be balloon-expandable. However, it is also contemplated that the stent 12 can be self-expandable using any conventional methods. In an exemplary aspect, the stent 12 can be expandable to an expanded configuration. In this aspect, it is contemplated that, in the expanded configuration, the inner surface of the stent 12 can define a substantially circular cross-sectional profile, such as shown in FIG. 2. It is further contemplated that the stent can be configured to deform such that the inner surface of the stent defines a non-circular cross-sectional profile, such as, for example and without limitation, an elliptical cross-sectional profile or an asymmetric cross-sectional profile. As used herein, the term "asymmetric cross-sectional profile" includes any non-circular cross-sectional shape. In a further aspect, it is contemplated that, in the expanded configuration, the inner surface of the stent 12 can define a substantially elliptical cross-sectional profile.

In exemplary aspects, the stent 12 can be generally tubular. It is contemplated that the stent 12 can comprise conventional stent materials, including, for example and without limitation, Nitinol, stainless steel, cobalt aluminum, deformable plastic, and the like. In various aspects, when the stent 12 is expandable, it is further contemplated that the stent can comprise a shape-memory material that is configured to expand the stent into an expanded configuration in which the inner surface of the stent defines a desired cross-sectional profile, such as, for example and without limitation, a circular cross-sectional profile, an elliptical cross-sectional profile, and the like.

Figure 15:
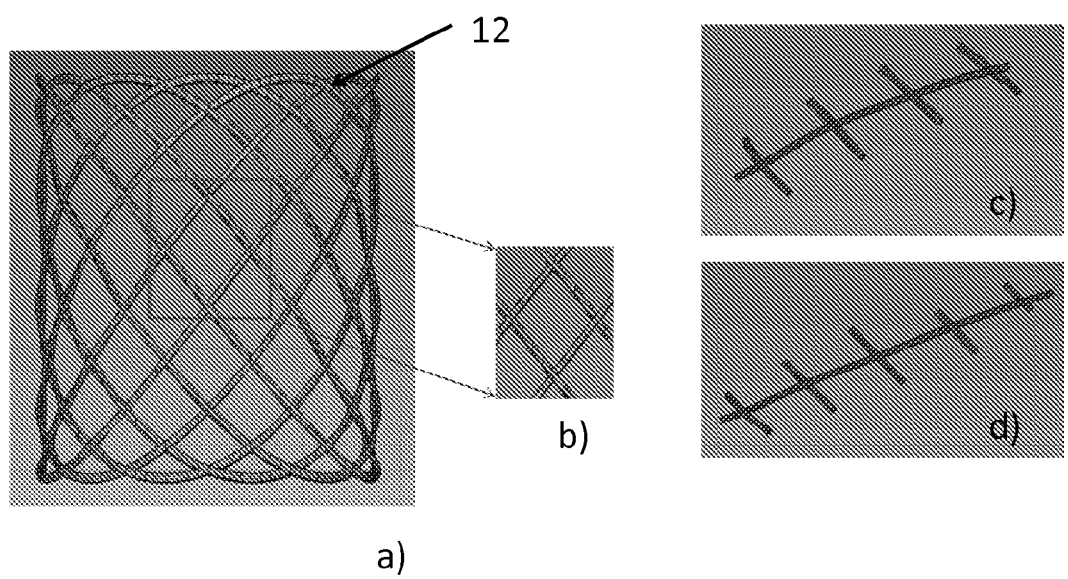
FIG. 15 displays an exemplary mesh design for a collapsible stent for use in a prosthetic heart valve as described herein.

Optionally, in an additional aspect, the stent 12 can have a mesh structure, as shown in FIG. 15. In one aspect, the mesh structure of the stent 12 can be laser-cut. Alternatively, in another aspect, it is contemplated that the stent 12 can have a woven mesh structure. In an exemplary aspect, the mesh structure can be woven from a single strand wire. In another exemplary aspect, the mesh structure can comprise an over-and-under pattern whereby intersecting and/or adjacent wires of the stent can slide past one another while maintaining the over-and-under pattern. In this aspect, unlike current commercially available stents, the joints or crossover points between intersecting wires of the stent 12 are not fixed. Thus, following implantation within the selected channel of the heart of the subject, it is contemplated that the initial cylindrical shape of the stent 12 can be easily deformed into an elliptical (or other) shape while still maintaining the required structural properties of the stent. Exemplary wire weaving techniques for making the stent 12 are shown in FIG. 15, in which the struts of the stent are depicted as generally having a diamond shape. However, it is contemplated that any conventional method for forming a mesh structure can be used to form the stent 12. In exemplary aspects, the stent 12 can have a plurality of peaks at its ends.

In an expanded position, as shown in FIG. 2 for example, the stent 12 can have an outer diameter ranging from about 11 mm to about 42 mm, and, more preferably, from about 14 mm to about 34 mm. In a particular exemplary aspect, the stent 12 can have an outer diameter of about 23 mm. However, it is contemplated that the stent 12 can have any operative outer diameter that permits proper positioning of the stent within the selected channel of the heart of the subject.

It is contemplated that the diameter of the stent 12, the spacing between parallel wires and/or adjacent openings within the mesh pattern of the stent, and the mechanical properties of the stent can be selectively varied as necessary to achieve a desired position and/or desired performance characteristics within the selected chamber of the heart of the subject. In exemplary aspects, the spacing between parallel wires and/or the dimensions of adjacent openings within the mesh pattern of the stent 12 are not uniform throughout the stent 12. It is further contemplated that the stent 12 can be configured for deformation to an elliptical shape. It is still further contemplated that the mesh configuration of the stent 12 can provide sufficient structural integrity to prevent collapse of the stent upon exposure to compression loading during valve closure, such as, for example and without limitation, aortic valve closure. It is still further contemplated that the stent 12 can be configured to accommodate and tolerate sufficient radial expansion force to permit secure positioning of the stent on an aortic root (or other valvular root) within the heart of the subject.

In another aspect, and with reference to FIG. 2, the prosthetic heart valve 10 can comprise a plurality of leaflets 20 positioned within the interior region 14 of the stent 12. In this aspect, and with reference to FIGS. 2 and 13, each leaflet 20 of the plurality of leaflets can define a free edge 22, an attachment edge 24, and a pair of spaced commissure regions 26a, 26b. In another aspect, each leaflet 20 of the plurality of leaflets can further define a belly region 28 positioned therebetween the free edge 22, the attachment edge 24, and the commissure regions 26a, 26b. In this aspect, the belly region 28 of each leaflet can generally correspond to the centermost portion of the leaflet. It is contemplated that the attachment edge 24 of each leaflet 20 can be attached to the stent 12 in a desired pattern, such as, for example and without limitation, a substantially U-shaped pattern, a scallop-shaped pattern, a semi-lunar shaped pattern, and the like. It is further contemplated that each commissure region 26 of each respective leaflet 20 of the plurality of leaflets can be positioned proximate a commissure region of an adjacent leaflet. In one aspect, the plurality of leaflets 20 can comprise, for example and without limitation, two, three, or four leaflets. In this aspect, it is contemplated that the plurality of leaflets can comprise at least two, at least three, or at least four leaflets. In an exemplary aspect, when the plurality of leaflets 20 comprises three leaflets, the plurality of leaflets can be substantially equally circumferentially spaced about the stent by about 120 degrees to form a tri-leaflet valve.

Optionally, in a further aspect, the prosthetic heart valve 10 can further comprise a lining skirt (not shown). In this aspect, it is contemplated that the attachment edge 24 of each leaflet 20 can be secured to the stent 12 through a lining skirt positioned within the interior region 14 of the stent. It is further contemplated that the lining skirt can be collapsible and expandable with the stent 12.

In various exemplary aspects, it is contemplated that at least one leaflet 20 of the plurality of leaflets can have a substantially different size than another leaflet of the plurality of leaflets. In an exemplary aspect, and with reference to FIG. 5B, when the plurality of leaflets 20 comprises four leaflets, the plurality of leaflets can comprise a first pair of opposed leaflets and a second pair of opposed leaflets. In this aspect, the first pair of opposed leaflets can be of a first size, and the second pair of leaflets can be of a second size, with the first size being substantially different from the second size. In an exemplary aspect, it is contemplated that the leaflets 20 of the first and second pairs of leaflets can each have an operative surface area that is in contact with blood within the selected chamber of the heart of the subject when the valve 10 is in a closed position, with the leaflets of the first pair of leaflets having a first operative surface area and the leaflets of the second pair of leaflets having a second operative surface area. In this aspect, it is contemplated that the first operative surface area can be greater than the second operative surface area, with the ratio between the first operative surface area and the second operative surface area ranging from about 1.01:1 to about 2:1, and more preferably, being about 3:2.

In another aspect, the plurality of leaflets can cooperate to define an outer diameter and a collective height along the flow axis 11. In this aspect, it is contemplated that the outer diameter of the valve 10 can range from about 11 mm to about 40 mm and more preferably range from about 17 mm to about 32 mm. It is further contemplated that the collective height of the plurality of leaflets 20 can range from about 5 mm to about 20 mm and more preferably range from about 8 mm to about 15 mm. In an exemplary aspect, the outer diameter of the plurality of leaflets can be about 22 mm, and the collective height of the plurality of leaflets can be about 10.83 mm.

Optionally, in an additional aspect, as shown in FIGS. 10A-10D, the free edge 22 of at least one leaflet 20 of the plurality of leaflets can comprise an extended edge portion 23 that projects from the leaflet in the flow direction 11. In this aspect, it is contemplated that the extended edge portion 23 of the free edge 22 can promote and enhance leaflet coaptation proximate a center point 40 of the valve. It is further contemplated that the extended portion 23 of the free edge 22 can improve the closure characteristics of the free edges of adjacent valve leaflets 20. In an exemplary aspect, it is contemplated that each leaflet 20 of the plurality of leaflets can have an operative surface area that is configured for contact with blood within the selected channel of the heart of the subject when the valve 10 is in a closed position. In this aspect, it is contemplated that the presence of an extended edge portion 23 on a particular leaflet 20 can increase the operative surface area of the leaflet by about 5% to about 25% and, more preferably, by about 8% to about 16%. It is further contemplated that the extended edge portion 23 of the free edge 22 of each leaflet 20 can have any suitable shape, including, for example and without limitation, the straight rectangular, single-bell, double-bell, and oval shapes respectively depicted in FIGS. 10A-10D. In an exemplary aspect, and as shown in FIG. 11D, the extended edge portion 23 can comprise a plurality of spaced tabs that extend outwardly from the free edge 22. It is contemplated that the extended edge portions 23 can optionally be die cut from the same material used to form the leaflet 20.

In exemplary aspects, each leaflet of the plurality of leaflets can comprise a pliable material. It is contemplated that the leaflet 20 can comprise one or more biological tissues, including, for example and without limitation, native or chemically-treated pericardium or valve leaflet tissues from human, ovine, bovine, porcine, or equine donors. It is further contemplated that the leaflet material can comprise one or more man-made materials, such as, for example and without limitation, rubbers, polymers, and the like. In addition to the specific examples described above, it is understood that any conventional leaflet material can be used to produce the leaflets described herein.

Figure 3:
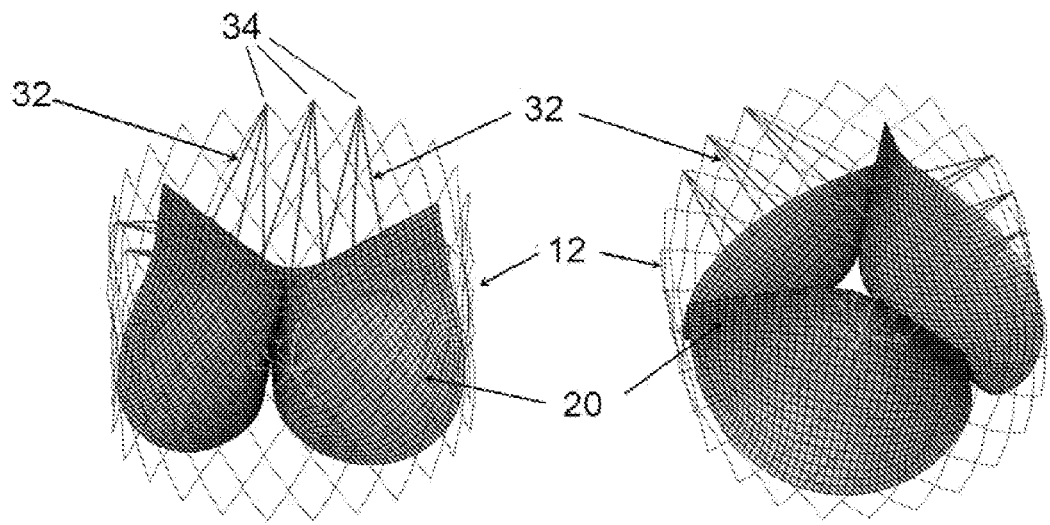
FIG. 3 displays perspective views of an exemplary prosthetic heart valve as described herein, showing three leaflets and a plurality of suspension members that are circumferentially attached to the expandable support stent and the leaflets.

In various aspects, it is contemplated that the prosthetic heart valve 10 can comprise a suspension assembly 30. As shown in FIG. 3, in one aspect, the prosthetic heart valve 10 can comprise a plurality of elongate suspension members 32 secured thereto the collapsible stent 12 at a plurality of attachment points 34. In this aspect, each attachment point of the plurality of attachment points can be spaced from the plurality of leaflets 20 in the flow direction 11. In exemplary aspects, the plurality of attachment points 34 can be positioned substantially within a common plane when the valve 10 is in an unloaded state. In these aspects, it is contemplated that the common plane can be substantially perpendicular to the flow axis 11. In an additional aspect, it is contemplated that the plurality of attachment points 34 can be positioned at any suitable location on the stent 12, including, for example and without limitation, a strut bar of the stent, a cross-over region of the stent, and a peak defined at an end of the stent (see FIG. 2). In a further aspect, it is contemplated that at least one suspension member 32 of the plurality of suspension members can be secured to each leaflet 20 of the plurality of leaflets.

Figure 4:
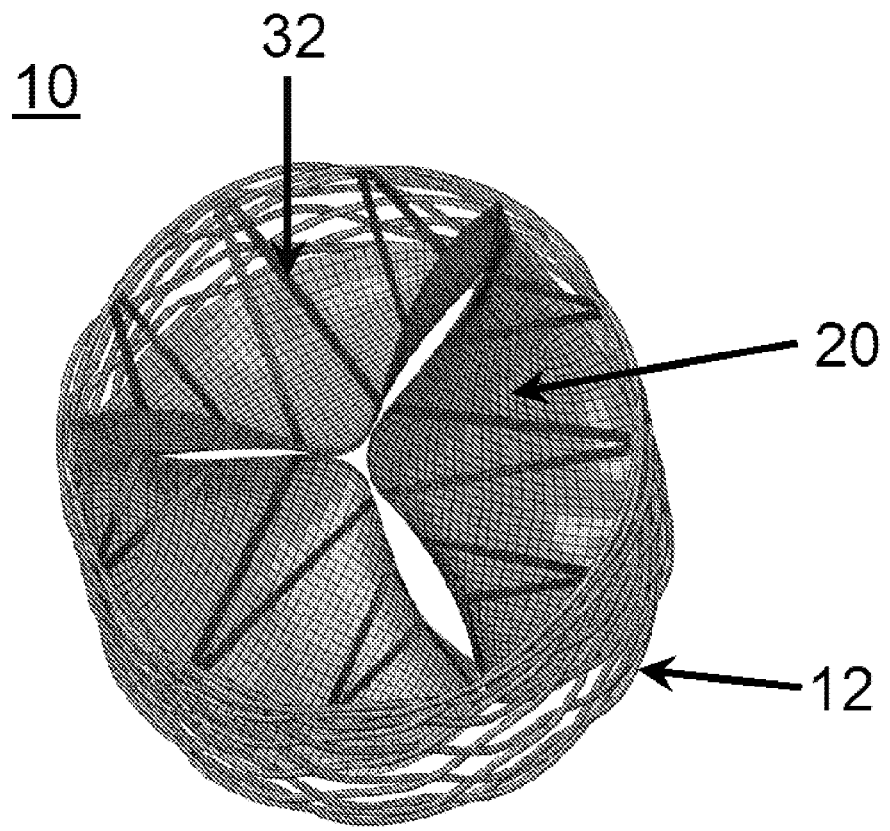
FIG. 4 is a perspective view of an exemplary prosthetic heart valve as described herein, showing three leaflets and a plurality of suspension members circumferentially attached to the expandable support stent and the leaflets.
Figure 11:
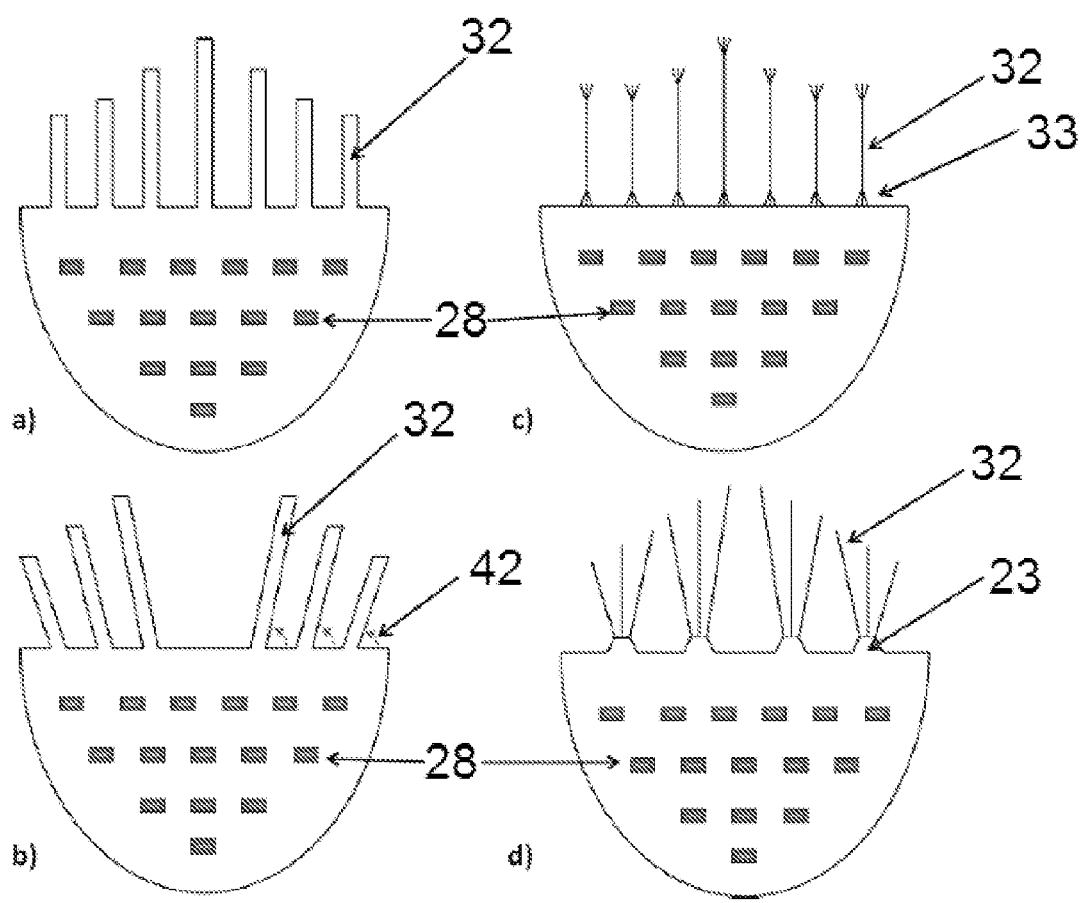
FIGS. 11A-11D are two-dimensional flat form depictions of exemplary suspension members connected to prosthetic valve leaflets as described herein. The suspension members can be inserted or attached to the leaflets through a variety of attachment methods.

In one aspect, as shown in FIGS. 3, 11C, and 11D, the plurality of suspension members 32 can comprise a plurality of narrow strands having a minimal diameter. However, in an additional aspect, as shown in FIGS. 4, 11A, and 11B, it is contemplated that the plurality of suspension members 32 can comprise a plurality of strip-like suspension members of increased thickness and/or diameter. In various exemplary aspects, it is contemplated that at least one suspension member 32 of the plurality of suspension members can have an end portion comprising a plurality of branch members 33 that are attached to one or more leaflets 20, such as shown in FIG. 11. In these aspects, it is contemplated that the plurality of branch members 33 at the end portion of the suspension member 32 can comprise from 2 to 8 branch members. It is contemplated that, through branching of the suspension members, the stress placed on the leaflets can be distributed and further reduced at points of contact between the suspension members 32 and the leaflets 20.

When the free edge 22 of a leaflet 20 comprises an extended edge portion 23 as described herein, it is contemplated that at least one suspension member 32 can be attached to the extended edge portion of the leaflet. It is contemplated that the extended edge portions 23 of the leaflets 20 can be configured to more readily permit attachment of the suspension members 32 to the leaflets while enhancing coaptation of the leaflets, particularly in exemplary applications when the valve 10 is deployed into a calcified valve root and resulting in an asymmetric valve geometry.

In exemplary aspects, it is contemplated that the suspension members 32 described herein can be integrally formed with a leaflet 20 as shown in FIG. 11. In these aspects, it is contemplated that a plurality of suspension members 32 can be formed by die-cutting the suspension members from the same material used to form the leaflet 20 to which the suspension members 32 are attached. It is further contemplated that the number of suspension lines that are integrally formed with a selected leaflet 20 can range from 3 to 12.

Figure 12:
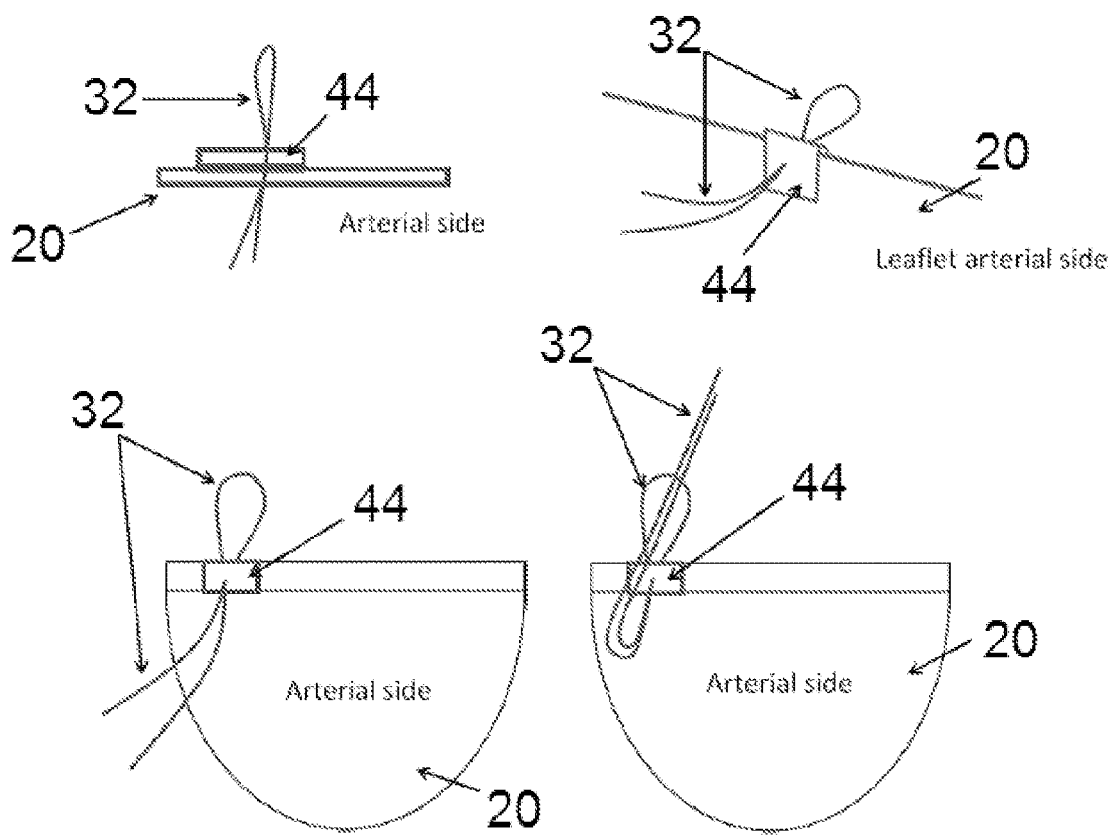
FIG. 12 displays an exemplary technique for attaching the suspension members to the prosthetic valve leaflets as described herein.
Figure 13:
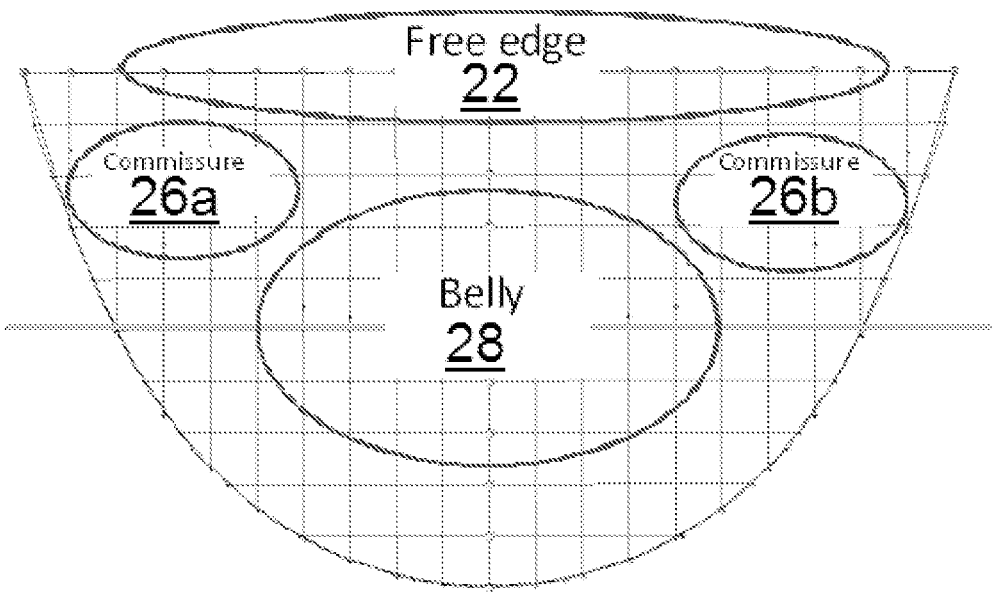
FIG. 13 is a schematic diagram generally displaying the locations of the free edge, commissure regions, and belly region of a leaflet of a prosthetic heart valve as described herein.

The plurality of suspension members 32 can be attached to the leaflets 20 using any conventional surgical attachment methods. An exemplary method for attaching the plurality of suspension members 32 to the free edge 22 of a leaflet 20 is depicted in FIG. 12. In one aspect, the method of attaching the suspension members 32 to the free edge 22 comprises providing an attachment structure 44 proximate the free edge, passing a suspension member through an insertion point in the attachment structure 44 and through the leaflet 20, then passing the suspension member back through the leaflet and again through the insertion point in the attachment structure, leaving a small loop formed by the suspension member on a ventricular side of the leaflet and two strands of the suspension member extending out of the insertion point in the attachment structure. Both free strands of the suspension member are then run through the loop and pulled toward the stent 12. In exemplary aspects, the attachment structure can be a substantially flat piece of material. In these aspects, it is contemplated that the attachment structure 44 can be a rectangular sheet that is formed from a material similar to the material of the leaflet 20. An alternative method for attaching the suspension member 32 to the free edge 22 of a leaflet 20 comprises folding an attachment structure as described herein such that it imposes on both ventricular and arterial sides of the leaflet edge.

In exemplary aspects, at least two suspension members 32 of the plurality of suspension members are secured to each leaflet 20 of the plurality of leaflets. FIGS. 6A-6E show exemplary prosthetic heart valves 10 in which 2, 3, 4, 5, and 6 suspension members are attached to each leaflet 20 of the plurality of leaflets. It is contemplated that any number of suspension members 32 can be attached to each leaflet 20 of the plurality of leaflets. It is further contemplated that the number of suspension members 32 that are attached to each respective leaflet 20 can vary among the plurality of leaflets.

In another aspect, at least one suspension member 32 of the plurality of suspension members can be secured to each commissure region 26a, 26b of at least one leaflet 20 of the plurality of leaflets. Optionally, in this aspect, it is contemplated that at least one suspension member 32 of the plurality of suspension members can be secured to each commissure region 26a, 26b of each leaflet 20 of the plurality of leaflets.

In another aspect, at least one suspension member 32 of the plurality of suspension members can be secured to the free edge 22 of at least one leaflet 20 of the plurality of leaflets. Optionally, in this aspect, it is contemplated that at least one suspension member 32 of the plurality of suspension members can be secured to the free edge 22 of each leaflet 20 of the plurality of leaflets.

In another aspect, at least one suspension member 32 of the plurality of suspension members can be secured to the belly region 28 of at least one leaflet 20 of the plurality of leaflets. Optionally, in this aspect, it is contemplated that at least one suspension member 32 of the plurality of suspension members can be secured to the belly region 28 of each leaflet 20 of the plurality of leaflets. In an exemplary aspect, at least two suspension members 32 of the plurality of suspension members can be secured to the belly region of one or more selected leaflets 20 of the plurality of leaflets. In exemplary aspects, as shown in FIG. 17, the plurality of suspension members 32 can attached to the belly region 28 and/or the commissure regions 26a, 26b of a leaflet in a variety of configurations. The configurations of the suspension members 32 displayed in FIG. 17 are merely exemplary, as it is contemplated that any configuration of suspension members can be used, provided the suspension members provide sufficient compliance and structural support to the leaflets of the valve.

In exemplary aspects, it is contemplated that the lengths of respective suspension members 32 secured to a particular leaflet 20 can be unequal. For example, when the suspension members 32 are operatively coupled to the stent 12 at a plurality of attachment points positioned within a common plane, it is contemplated that, as a leaflet 20 closes, the center of the free edge 22 of the leaflet will be farther away from the common plane than the portions of the free edge that are proximate the commissure regions 26a, 26b of the leaflet. It is further contemplated that at least one suspension member 32 of the plurality of suspension members can be formed from a different material than another suspension member of the plurality of suspension members. Thus, it is contemplated that the lengths and/or materials of respective suspension members 32 can be selectively varied depending on the particular location at which each suspension member is secured to a particular leaflet to achieve maximum stress reduction on the leaflet and/or optimize coaptation of the leaflets.

Figure 5A:
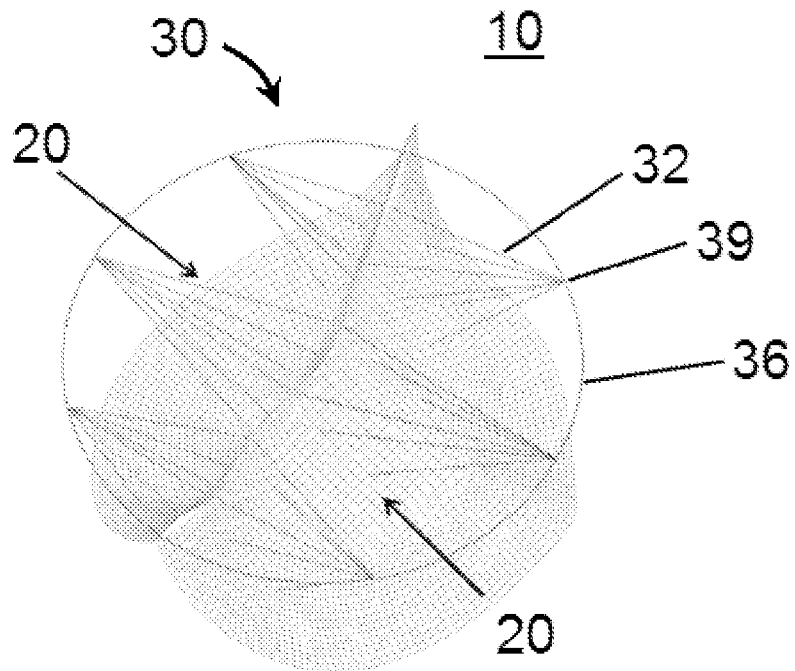
FIG. 5A is a perspective view of an exemplary prosthetic heart valve as described herein, having two leaflets and a plurality of suspension members circumferentially coupled to the expandable support stent (not shown) and the leaflets.
Figure 5B:
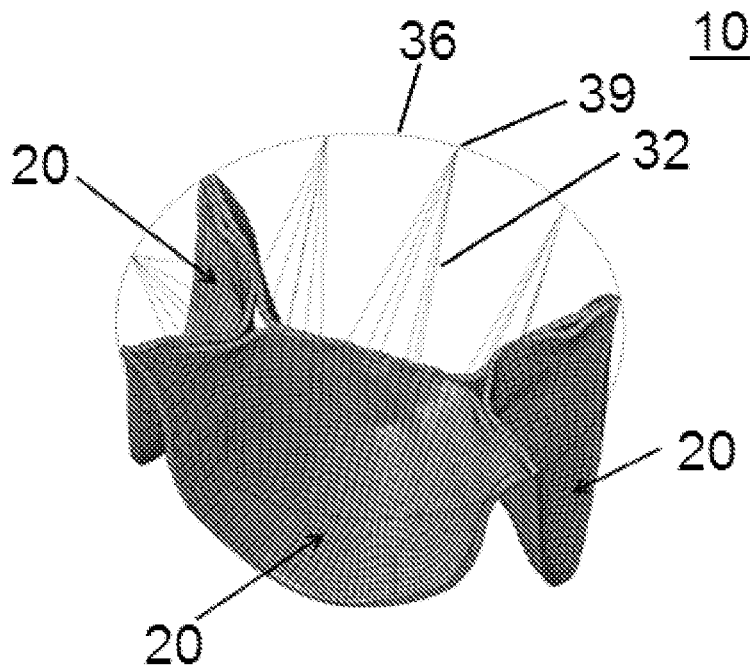
FIG. 5B is a perspective view of an exemplary prosthetic heart valve as described herein, having four leaflets and a plurality of suspension members circumferentially coupled to the expandable support stent (not shown) and the leaflets. The leaflets can be symmetrically or asymmetrically arranged circumferentially about the circumference of the supporting stent.
Figure 5C:
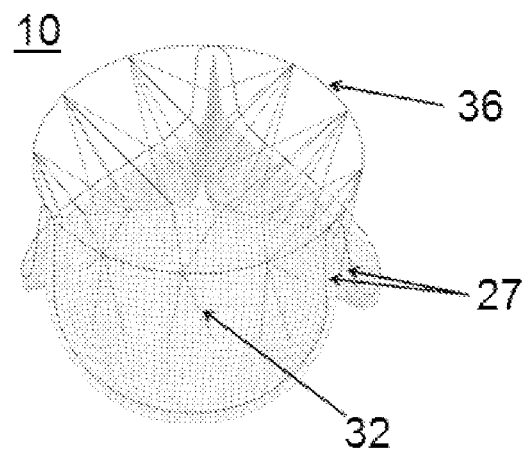
FIG. 5C is a perspective view of an exemplary non-collapsible prosthetic heart valve as described herein, having three leaflets and a plurality of suspension members circumferentially coupled to the expandable support stent (not shown) and the leaflets.
Figure 6A:
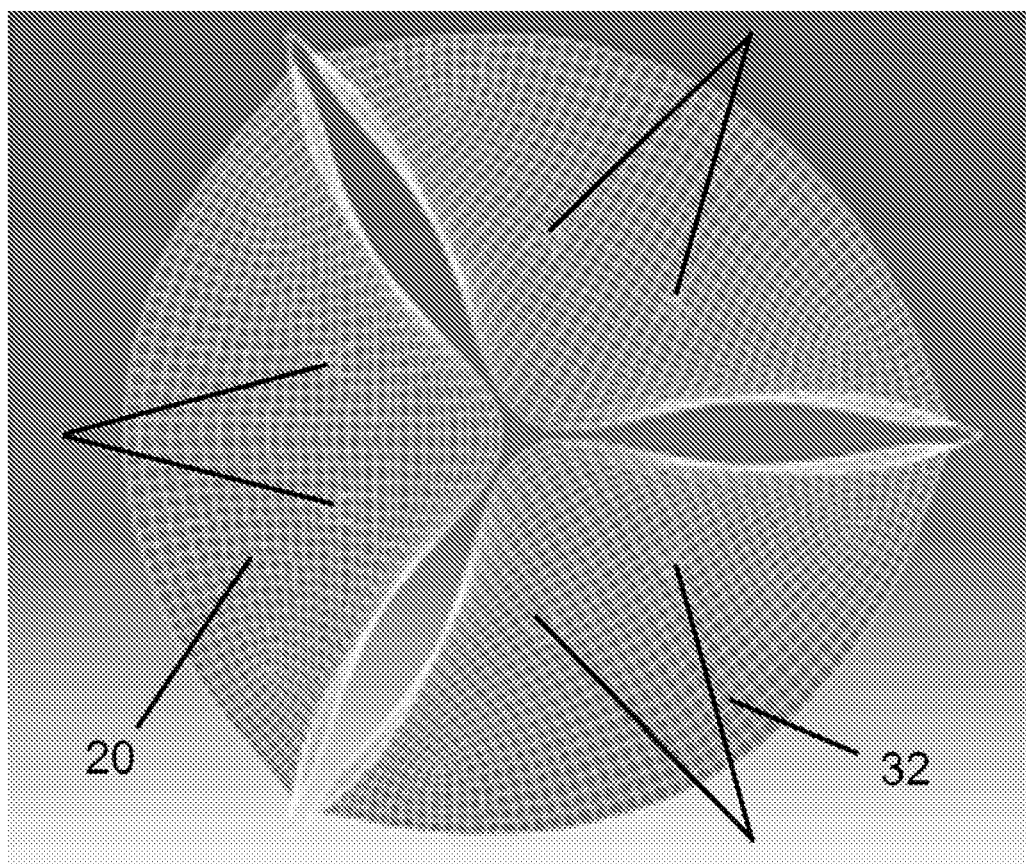
FIGS. 6A-6E are top views of exemplary prosthetic heart valves as described herein respectively showing two suspension members attached to each leaflet of the valve, three suspension members attached to each leaflet of the valve, four suspension members attached to each leaflet of the valve, five suspension members attached to each leaflet of the valve, and six suspension members attached to each leaflet of the valve.
Figure 6B:
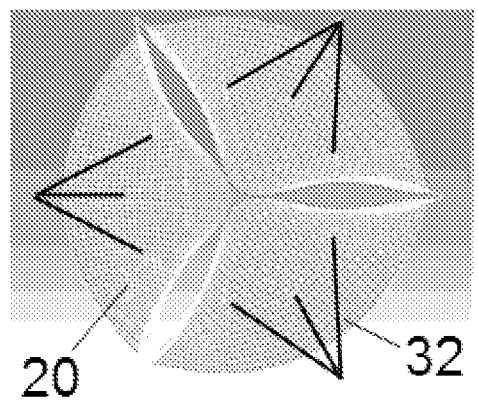
Figure 6C:
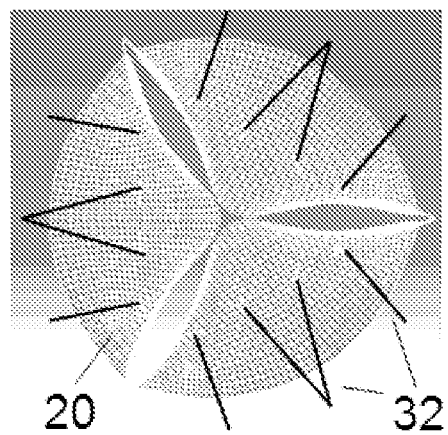
Figure 6D:
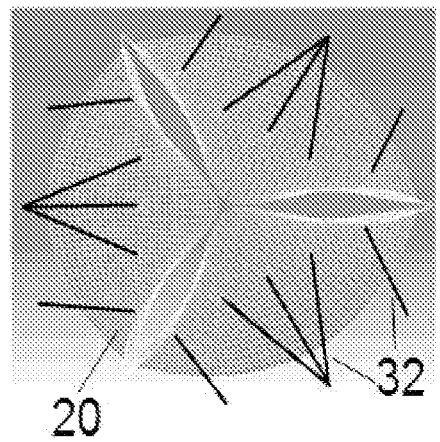
Figure 6E:
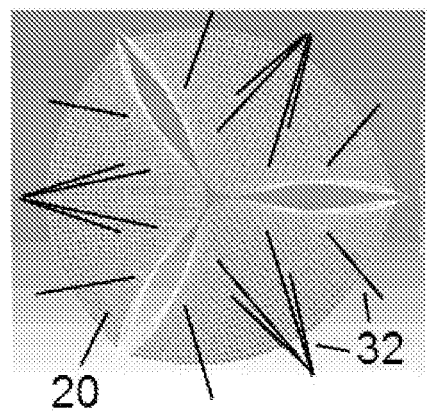

As shown in FIG. 5C, it is contemplated that the plurality of suspension members 32 can be operatively coupled or secured to a plurality of commissure posts 27 that connect adjoining commissure regions of adjacent leaflets and that are positioned within the valve 10. In additional aspects, it is contemplated that the plurality of suspension members 32 can be connected to the surrounding native valve tissues. For example, when the selected channel within the heart of the subject is the aorta, it is contemplated that the plurality of suspension members 32 can be connected to the aortic sinus and/or ascending aorta.

Figure 7:
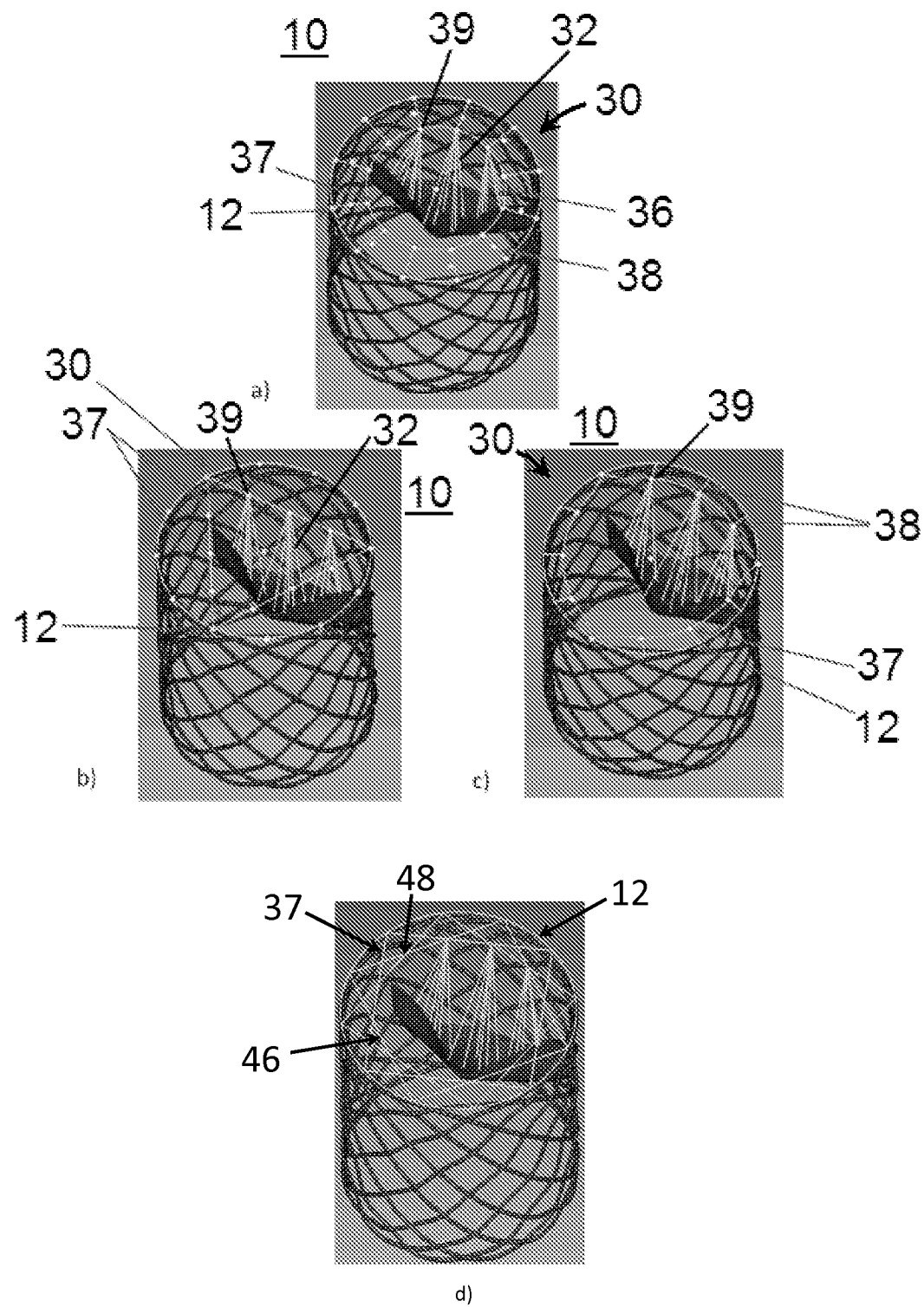
FIGS. 7A-7D are perspective views of exemplary suspension assemblies in which a plurality of suspension members are connected axially between a support structure and the leaflets.
Figure 8A:
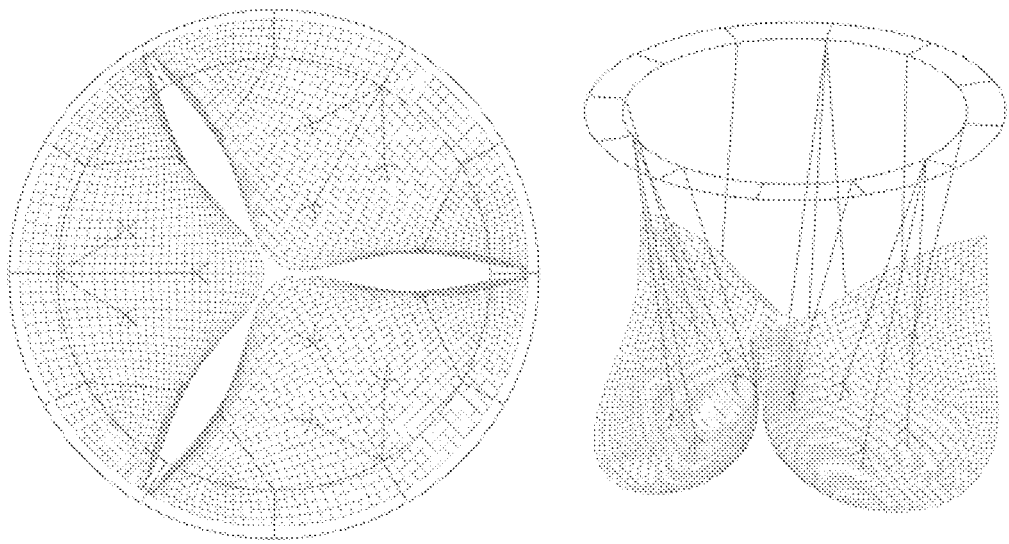
FIG. 8A displays top and side perspective views of a suspension member having a substantially circular central support structure as shown in FIG. 7A.
Figure 8B:
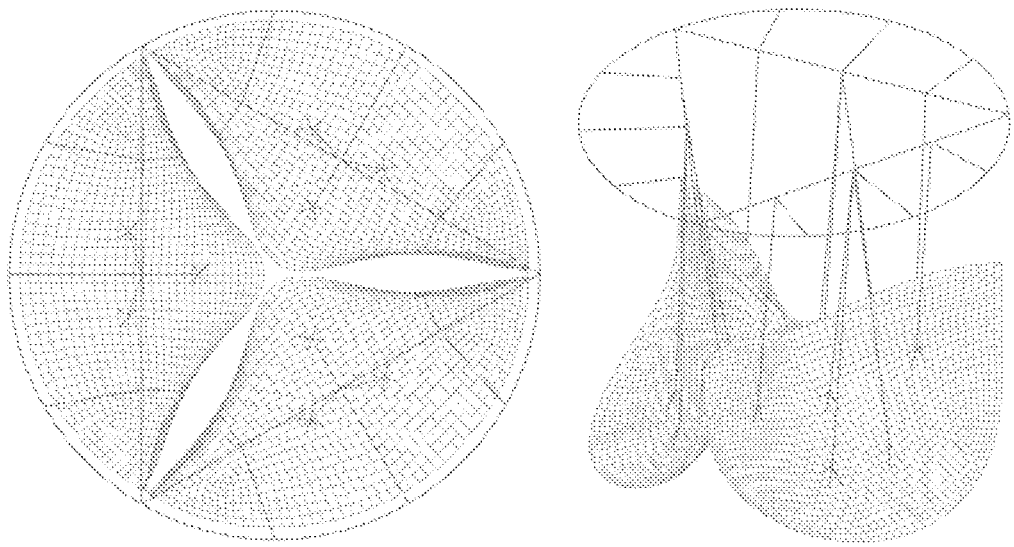
FIG. 8B displays top and side perspective views of a suspension member having a substantially triangular central support structure as shown in FIG. 7B.
Figure 8C:
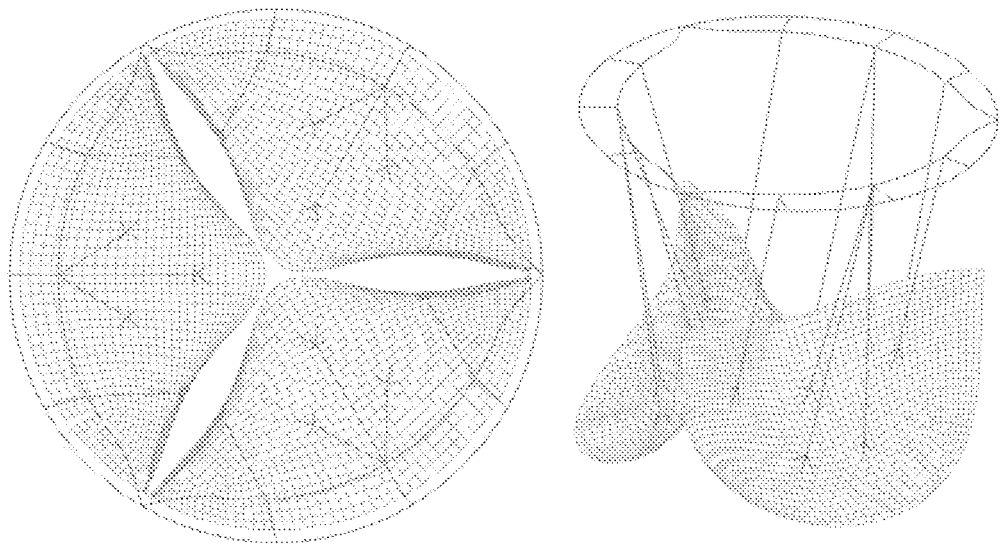
FIG. 8C displays top and side perspective views of a suspension member having a substantially bell-shaped central support structure as shown in FIG. 7C.
Figure 8D:
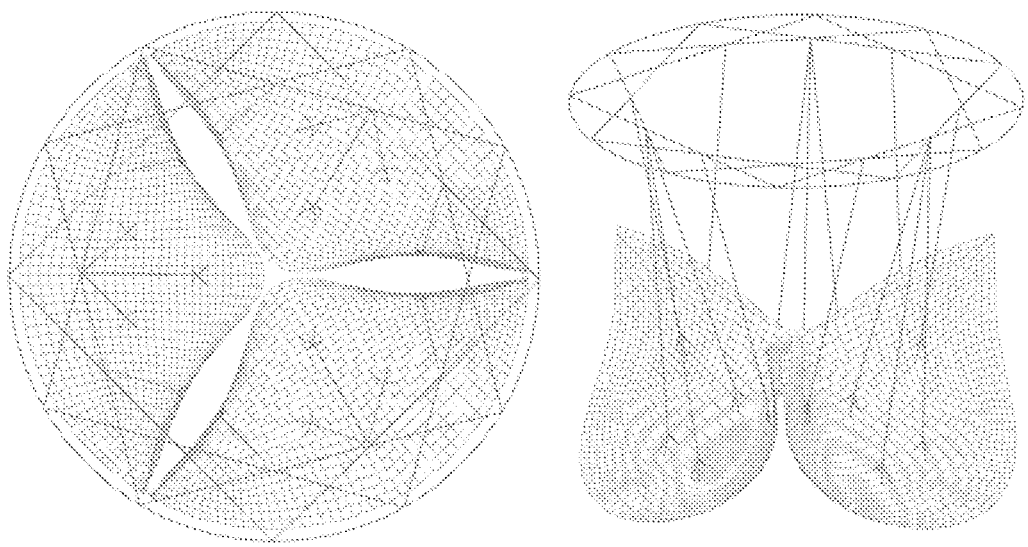
FIG. 8D displays top and side perspective views of a suspension member having a substantially star-patterned mesh-like central support structure as shown in FIG. 7D.
Figure 9A:
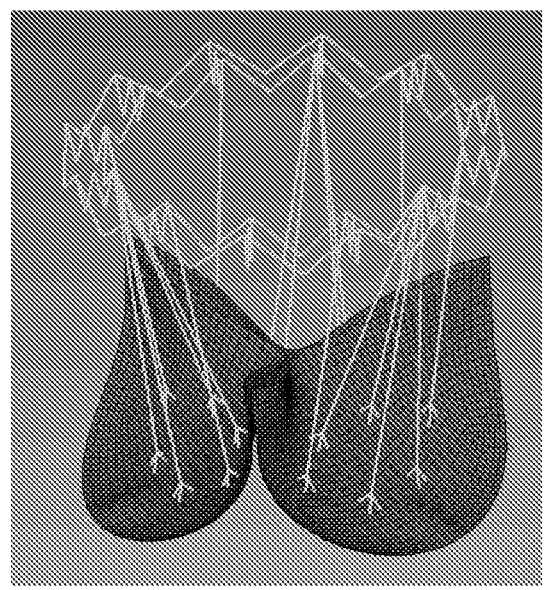
FIGS. 9A-9B display perspective and side views of an exemplary collapsible suspension assembly having a circular central support structure as described herein.
Figure 9B:
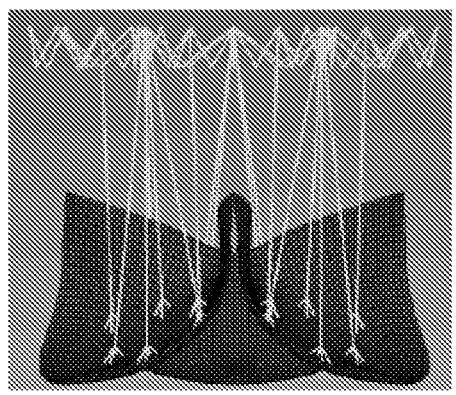
Figure 9C:
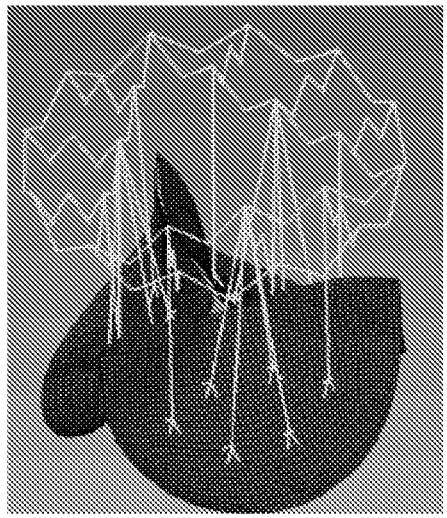
FIG. 9C displays a perspective view of an exemplary collapsible suspension assembly having a triangular central support structure as described herein.
Figure 9D:
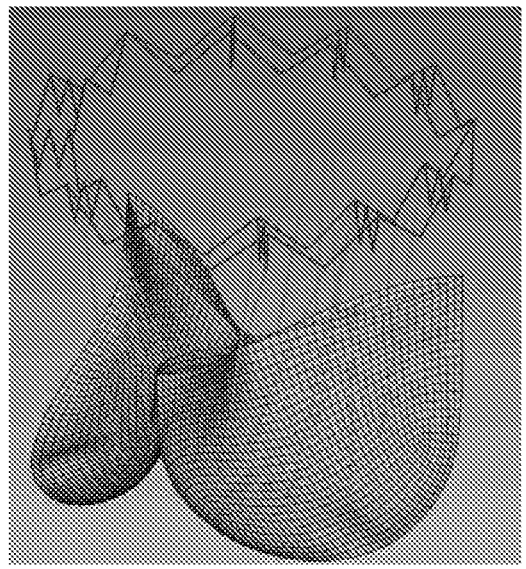
FIG. 9D displays a perspective view of an exemplary collapsible suspension assembly having a substantially bell-shaped central support structure as described herein.
Figure 16:
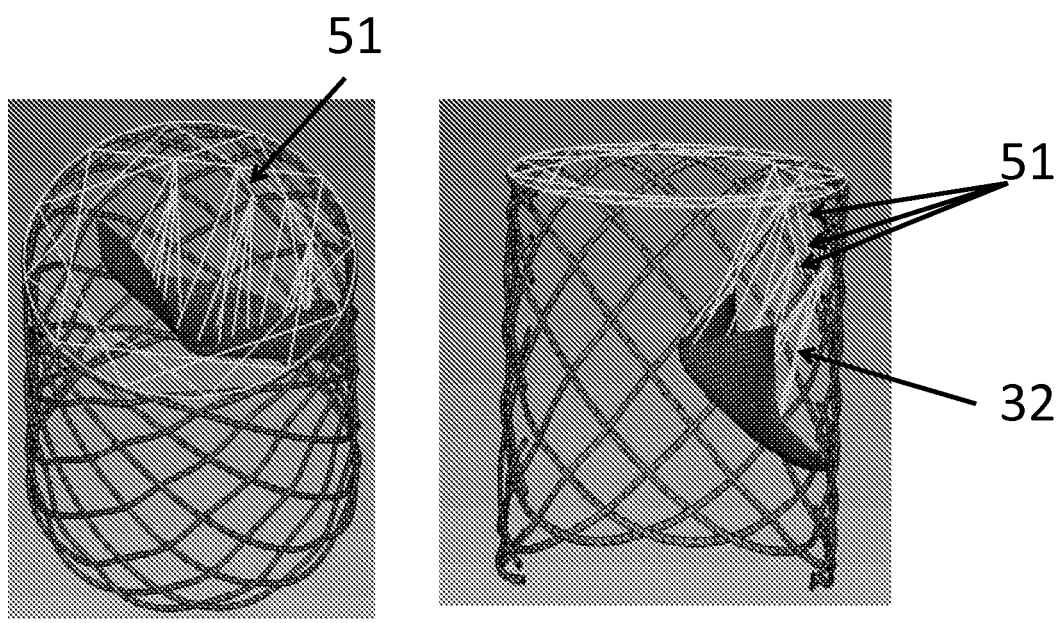
FIG. 16 displays an exemplary sub-structure of the central support structure connecting to portions of the stent that extend to a point that is spaced in a direction opposite the direction of blood flow from at least one commissure region of a leaflet of the valve as described herein.
Figure 17A:
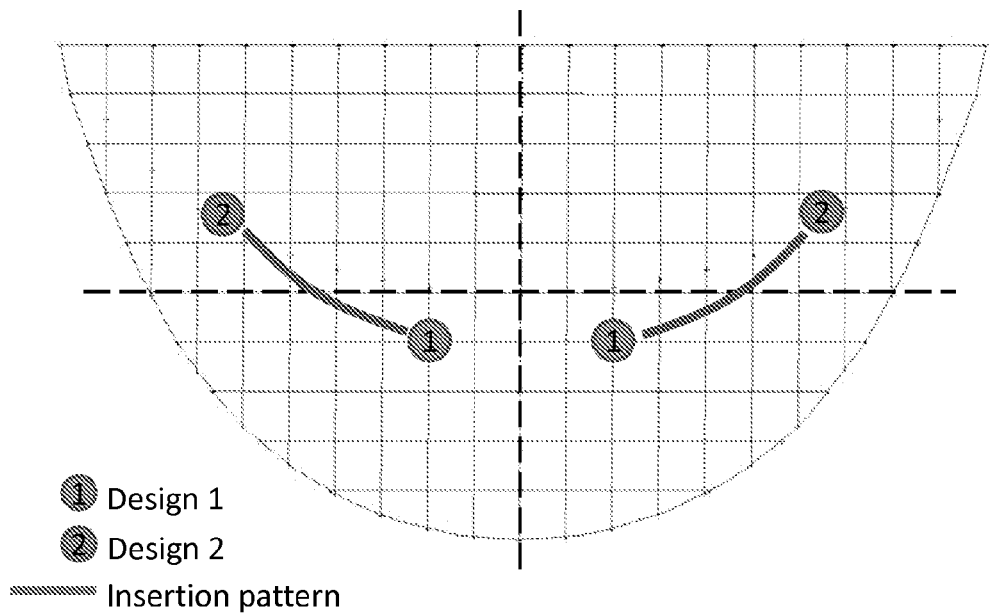
FIG. 17 displays a variety of exemplary configurations for attachment of suspension members to the belly region and commissure regions of a leaflet as described herein.
Figure 17B:
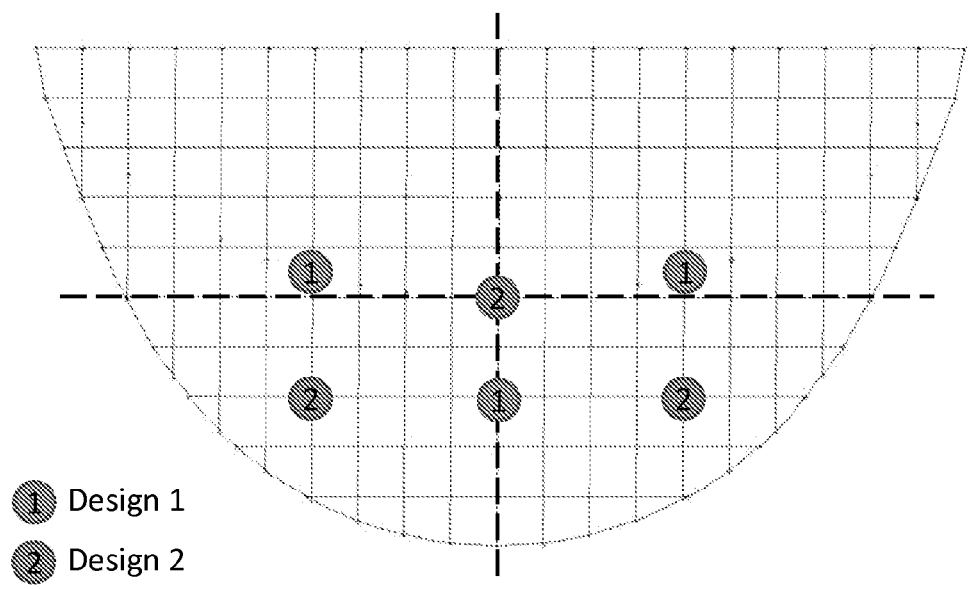
Figure 17C:
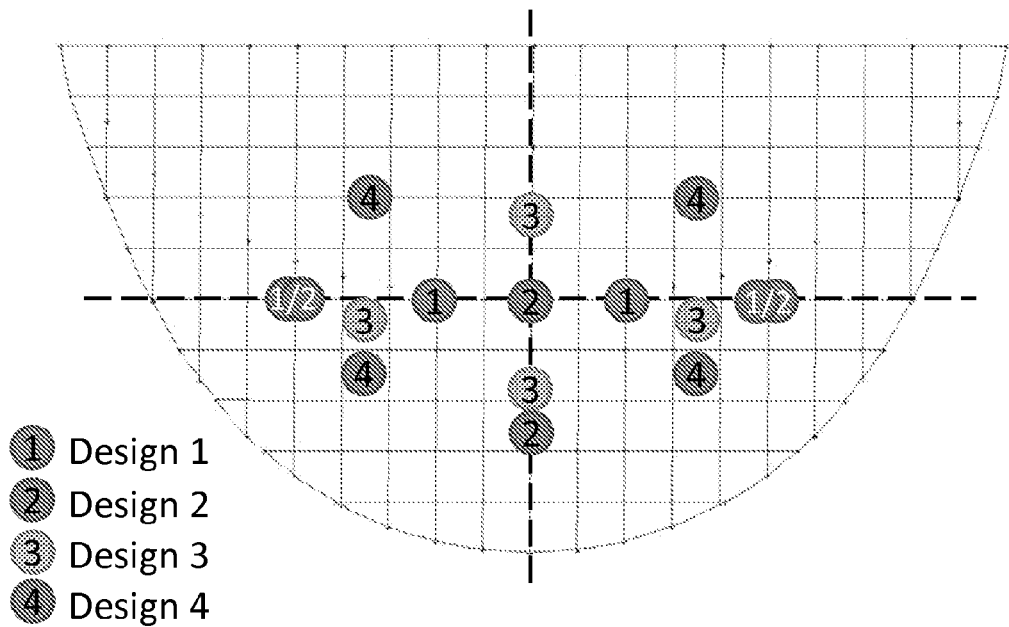
Figure 17D:
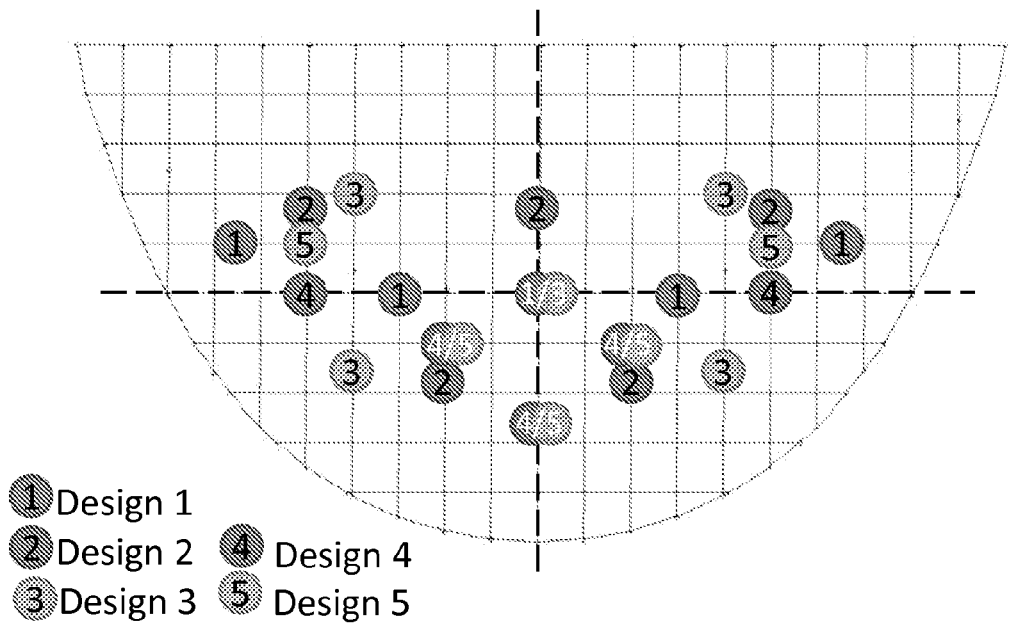
Figure 17E:
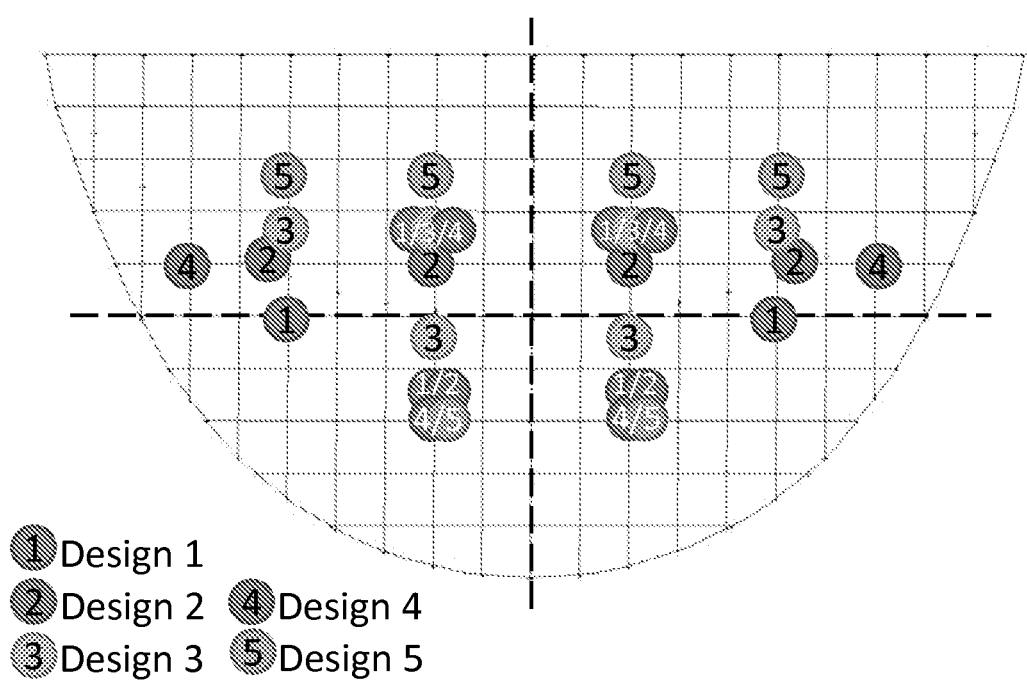

Optionally, in various aspects, and with reference to FIGS. 7-9, the suspension assembly 30 can further comprise a central support structure 37 coupled thereto the collapsible stent 12 such that the central support structure is spaced from the free edges 22 of the plurality of leaflets 20 in the flow direction 11. It is contemplated that the central support structure 37 can be spaced from the free edges 22 of the plurality of leaflets 20 in the flow direction 11 by at least 1 mm. In these aspects, and as shown in FIG. 16, it is contemplated that the suspension assembly 30 can further comprise at least one sub-structure 51 that extends from the central support structure 37 to a point on the stent 12 that is spaced from the central support structure 37 in a direction opposite the flow direction 11. In an exemplary aspect, the at least one sub-structure 51 can extend from the central support structure 37 to a point on the stent 12 that is spaced in a direction opposite the flow direction 11 from at least one commissure region 26 of a leaflet 20 of the valve 10 as described herein (such that, along the flow axis, the commissure region 26 is positioned between the central support structure and a distal end point of the sub-structure). Thus, in exemplary applications in which the selected channel within the heart of the subject is the aorta, the at least one sub-structure 51 can extend to a point below at least one commissure region 26 of a leaflet 20 of the valve 10. height of the leaflet commissures. It is contemplated that at least one suspension member 32 of the plurality suspension members can be secured directly to a sub-structure 51, thereby coupling the at least one suspension member 32 (and the attached leaflet) to the stent 12 and the central support structure 37. It is contemplated that the at least one sub-structure 51 and the central support structure 37 can comprise similar materials and/or possess similar mechanical properties.

When the valve 10 comprises a lining skirt, it is contemplated that the central support structure 37 can be coupled thereto the stent 12 through the lining skirt. In these aspects, rather than being secured to the stent 12, the plurality of suspension members 32 are secured to the central support structure 37 of the suspension assembly 30. In these aspects, it is contemplated that the entire suspension assembly 30, including the central support structure 37 and the plurality of suspension members 32, can be collapsible and expandable with the stent 12.

In exemplary aspects, as shown in FIG. 7, the central support structure 37 of the suspension assembly 30 can be coupled to the stent 12 by a plurality of connecting members 38. In these aspects, it is contemplated that the connecting members 38 can have any structure, such as, for example, a straight element, a beam, a string, or a spring, that imparts elasticity and/or damping characteristics to the suspension members 32. It is further contemplated that the connecting members 38 can be configured to pull the central support structure 37 toward the inner surface of the stent 12. In one aspect, as shown in FIG. 7A, at least a portion of the central support structure 37 can be spaced from the inner surface of the stent 12. In this aspect, it is contemplated that the entire central support structure 37 can be substantially uniformly spaced from the inner surface of the stent 12. In another aspect, as shown in FIG. 7B, at least a portion of the central support structure 37 can be directly secured to the stent 12 and/or a liner coupled to the stent. In a further aspect, as shown in FIG. 7C, at least a portion of the central support structure 37 can be spaced from the inner surface of the stent 12 and at least a portion of the central support structure can be directly secured to the stent. In exemplary aspects, as shown in FIG. 7A, the central support structure 37 can be substantially circular. In another exemplary aspect, as shown in FIG. 7B, the central support structure 37 can be substantially triangular. In still another exemplary aspect, as shown in FIG. 7C, the central support structure 37 can be substantially bell-shaped such that the central support member is substantially radially spaced from the blood flow jet exiting the prosthetic heart valve 10.

In a further aspect, and with reference to FIG. 7D, the central support structure 37 of the suspension assembly 30 can comprise a plurality of offset support members 46 that are spaced circumferentially about the inner surface of the valve such that each support member of the plurality of support members spans between two points on the inner surface of the valve and overlaps with at least one other support member at an intersection point 48. In this aspect, it is contemplated that at least one suspension member 32 of the plurality of suspension members can be secured to the central support structure 37 at an intersection point 48. In exemplary configurations, it is contemplated that the plurality of offset support members 46 can cooperate to form a star-patterned mesh-like structure, such as depicted in FIG. 7D. It is contemplated that the overlapping structure of support members 46 can impart advantageous structural integrity to the central support structure 37.

However, it is contemplated that the central support structure 37 can have any shape that permits attachment of the plurality of suspension members 32 to desired locations on the plurality of leaflets 20. Additional perspective views of exemplary valves having central support structures as described herein are provided in FIGS. 8A-8D.

As shown in FIG. 11, it is contemplated that, following implantation of the prosthetic heart valve 10 within the selected channel within the heart of the subject, at least one suspension member 32 of the plurality of suspension members can be angularly oriented relative to the free edge 22 of the leaflet 20 of the plurality of leaflets to which it is attached. It is further contemplated that, following implantation of the prosthetic heart valve 10 within the selected channel within the heart of the subject, at least one suspension member 32 of the plurality of suspension members can be substantially perpendicularly oriented relative to the free edge 22 of the leaflet 20 of the plurality of leaflets to which it is attached.

It is contemplated that, following implantation of the prosthetic heart valve 10 within the selected channel within the heart of the subject, the plurality of suspension members 32 can be configured to mechanically reinforce the plurality of leaflets 20, thereby reducing the stress experienced by the plurality of leaflets and improving durability of the plurality of leaflets. It is further contemplated that the plurality of suspension members 32 can be configured to enhance coaptation of the plurality of leaflets. In exemplary aspects, the plurality of suspension members can be configured to at least partially bear high systolic pressure loads experienced by the prosthetic heart valve 10 following implantation of the valve within the selected channel of the heart of the subject.

In exemplary aspects, it is contemplated that the plurality of leaflets 20 and the suspension assembly 30, including the plurality of suspension members 32, can be radially collapsible and expandable with the stent 12. In these aspects, it is contemplated that the plurality of leaflets and the plurality of suspension members, along with the central support structure, can permit deformation and/or expansion of the valve 10 into a configuration in which the valve has a substantially elliptical (or other non-circular) cross-sectional profile, generally defined by the inner surface of the stent 12. Exemplary collapsible central support structures 37 are shown in FIGS. 9A-9D. It is contemplated that an exemplary collapsible central support structure 37 can comprise a plurality of joints, and the central support structure can be foldable at the plurality of joints. In one aspect, it is contemplated that the suspension assembly 30 can further comprise an outer support structure 36 that is attached circumferentially along at least a portion of the valve 12. In this aspect, it is contemplated that the central support structure 37 can be coupled to the valve 12 through the outer support structure 36. For example, in exemplary aspects, at least one connecting member 38 can extend between the central support structure 37 and the outer support structure 36. It is contemplated that the outer support structure 36 can be collapsible and, as such, can optionally comprise a plurality of joints, with the outer support structure being foldable at the plurality of joints. It is further contemplated that each connecting member 38 extending between the central support structure 37 and the stent 12 and/or the outer support structure 36 can comprise at least one joint, thereby permitting collapse of the connecting member. In exemplary aspects, as shown in FIGS. 5A-5C, it is contemplated that the plurality of suspension members 32 can be coupled directly to the outer support structure 36 one or more attachment points 39, whether or not the suspension assembly 30 comprises a central support structure 37.

It is contemplated that the suspension assemblies 30 described herein can carry at least a portion of the hydrodynamic pressure loads placed on the prosthetic heart valve 10 during opening and closing of the leaflets 20. In contrast, known prosthetic valve designs place all of these hydrodynamic pressure loads on the leaflets. Thus, it is contemplated that the use of the suspension assemblies 30 described herein can reduce leaflet stresses and thereby prolong the service life and durability of the prosthetic heart valve 10.

It is further contemplated that the suspension assembly 30 can be configured to impart desired compliance characteristics to the prosthetic heart valve 10. Optionally, in one aspect, at least one suspension member 32 of the plurality of suspension members can comprise a compliant material. In this aspect, it is contemplated that each suspension member 32 of the plurality of suspension members can comprise a compliant material. In another optional aspect, at least a portion of the central support structure 37 can comprise a compliant material. In this aspect, it is contemplated that substantially the entire central support structure 37 can comprise a compliant material. In exemplary aspects, each suspension member 32 of the plurality of suspension members and the central support structure 37 can comprise a compliant material. In further aspects, it is contemplated that the connection members 38 and/or the outer support structure 36 can comprise a compliant material. It will be appreciated that the entire suspension assembly 30 cooperates to impart a suitable level of compliance to the prosthetic heart valve 10. Thus, for example, it is contemplated that the same compliance can be achieved by providing any of the following: (a) a highly compliant central support structure 37 coupled with a plurality of non-compliant suspension members 32, (b) a plurality of highly compliant suspension members 32 coupled with a non-compliant central support structure 37; or (c) a central support structure 37 of intermediate compliance coupled with a plurality of suspension members of intermediate compliance. In additional aspects, it is contemplated that the compliance characteristics of individual suspension members 32 of the plurality of suspension members can be selectively varied to achieve a desired mechanical effect on the leaflets 20 of the valve 10. Further, it is contemplated that the compliance characteristics of the suspension assembly 30 can be selectively modified by adjusting the thickness, beam length, material used, initial slack, and/or pre-tension of one or more components of the suspension assembly. Examples of compliant materials as described herein included, for example and without limitation, synthetic polymers, non-degradable compounds, sutures, threads, nylon, thin and flexible metals, biologically derived tissues, native tissues, and the like.

In use, it is contemplated that the valve 10 can be deployed and positioned within the selected channel of the heart of the subject using conventional transcatheter procedures. However, it is contemplated that any known stent and/or valve delivery technique can be used to deploy and position the valve 10 within the selected channel of the heart of the subject.

In exemplary applications in which the selected channel of the heart of the subject is the aorta, it should be appreciated that the plurality of suspension members of the valve 10 as described herein do not replicate or mimic the physiological function of the native aortic valve. Whereas the native aortic valve lacks chordae or other structural support members such as are found in the atrioventricular (AV) valves, the prosthetic valve 10 described herein comprises a plurality of suspension members that impart structural support and compliance to the leaflets 20 of the prosthetic valve.

EXPERIMENTAL EXAMPLES

The following examples are put forth so as to provide those of ordinary skill in the art with a complete disclosure and description of how the prosthetic heart valves claimed herein are evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

The computational analyses disclosed herein were achieved using finite element software ABAQUS to model the response of a prosthetic heart valve under a physiological loading condition of 120 mmHg. The computational modeling method for simulation of heart valve deformation under quasi-static loading condition is disclosed in detail in Sun et al. 2005. Briefly, the three valve leaflets are modeled with large strain shell elements (ABAQUS element S4R, a four-node quadrilateral finite strain element with reduced integration, and S3R, a 3-node triangular finite strain element with reduced integration). Each leaflet has its own local coordinate system for definition of leaflet material properties. Uniform thickness of leaflets was assumed, which is appropriate for pericardial tissue. Implementation of the Fung-elastic material model in ABAQUS followed the method that has been previously described in Sun et al., "Simulated Bioprosthetic Heart Valve Deformation Under Quasi-Static Loading," Journal of Biomechanical Engineering 127: 905-914 (2005), the disclosure of which is incorporated herein by reference in its entirety. The contact between each two leaflets was modeled using the master-slave contact pair (an interaction in ABAQUS). The leaflet-stent attachment contour line of each leaflet was constrained in all three transitional degree of freedom (DOF). A quasi-static approach was used to analyze the deformation of PAV from unloaded to fully loaded and closed state by applying the uniform transvalvular pressure of 120 mmHg to the aortic side of the leaflet.

Example One

A previous simulation of a commonly used pericardial surgical valve has shown a peak maximum principal stress of 663.2 kPa (96.2 PSI) at the fully valve closure position. Another previous simulation has shown the peak maximum principal stress of a transcatheter valve at the fully closed position to be 915.62 kPa (131.7 PSI).

Computational models of prosthetic heart valves having a plurality of suspension members as described herein were conducted using the modeling procedure disclosed in Li, K., and Sun, W., 2010, "Simulated thin pericardial bioprosthetic valve leaflet deformation under static pressure-only loading conditions: Implications for percutaneous valves," Annals of Biomedical Engineering, 38(8), pp. 2690-2701, the disclosure of which is incorporated herein by reference in its entirety. In this analysis, the suspension members were connected between the free edge of the leaflets and the stent. Using the same material properties for the leaflets and under the same physiological pressure loading condition of 120 mmHg, the model with suspension structures has the peak maximum principal stress at the fully closed position of 623.3 kPa (90.4 PSI). It should be noted that the pericardial surgical valve has a clinical durability of 15-20 years. Current transcatheter valves have an estimated durability of about 5-7 years. To summarize the valve types, the associated analyzed peak stress and estimated durability in the below table:

| Valves | Peak Stress | Durability |
| --- | --- | --- |
| Known Pericardial Surgical Valve | 96 PSI | 15-20 years |
| Simulated transcatheter valve without suspension members | 132 PSI | about 5-7 years |
| Simulated transcatheter valve with suspension members | 90 PSI | TBD |

Example Two

Figure 14:
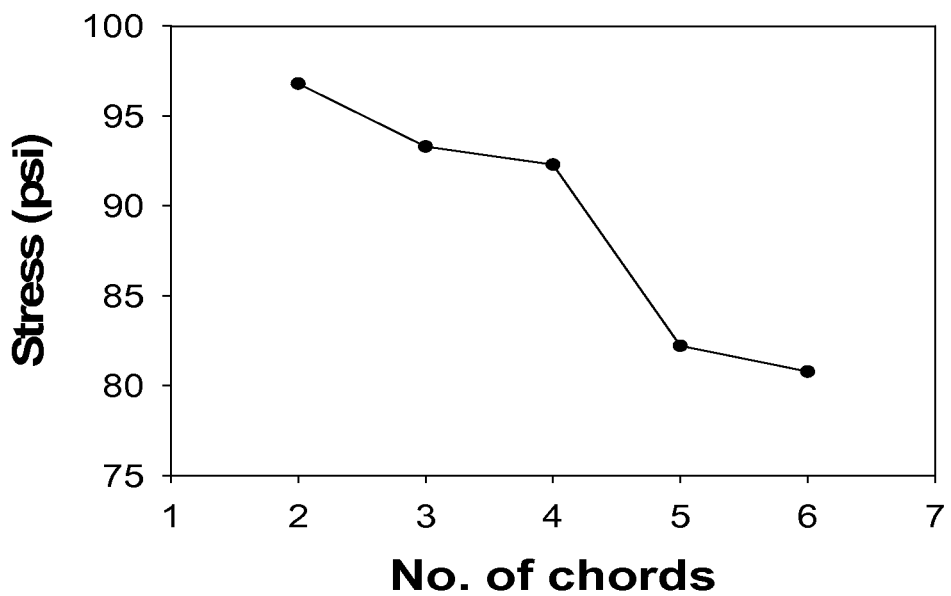
FIG. 14 displays a graph of stress on a leaflet relative to the number of suspension members attached to the leaflet.

Prosthetic heart valves as described herein having various numbers of suspension members attached to each respective leaflet of the valve were evaluated for leaflet stresses upon application of a uniform load. FIG. 14 displays the stress reduction as the number of suspension members attached to each respective leaflet was increased.

High peak stress on a surgical valve is known to occur at the commissure region and run across the belly region, creating a high stress band. The addition of suspension members near the commissure and/or belly regions reduced the stress within this band. As shown in FIG. 14, the addition of two suspension members to the belly region reduced stresses on the leaflet to measured values of 99.48 and 96.80 psi, equivalent to current simulated surgical valve stresses. One design for a three-suspension member per leaflet configuration brought the stress down to 89.43 psi. In this design, two suspension members were placed near the commissure regions. The 5-suspension member per leaflet configuration achieved an 82.22 psi leaflet stress. In this design, two suspension members were placed near the commissure regions and three suspension lines were placed on the belly region.

Example Three

Figure 18A:
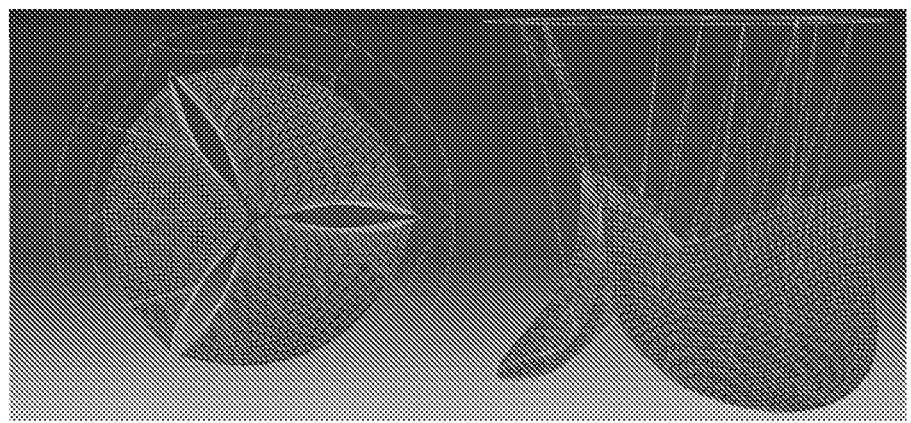
FIG. 18 displays two exemplary designs of suspension assemblies with suspension members attached to a central support structure.
Figure 18B:
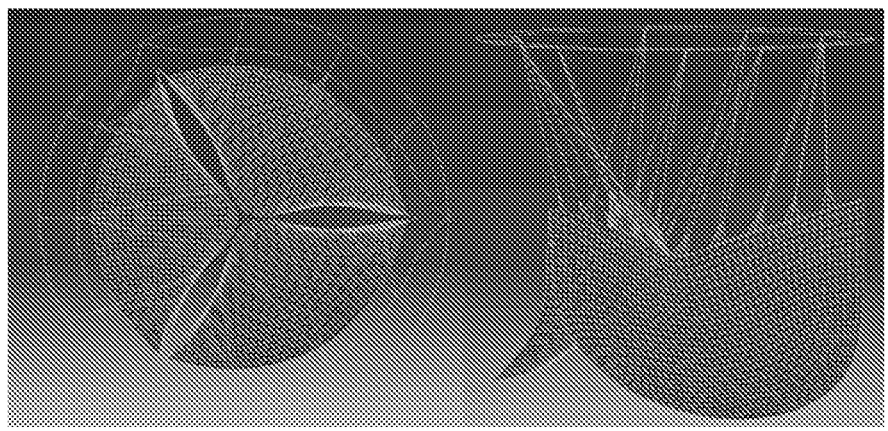

Two designs of suspension assemblies were chosen to demonstrate that the stress experienced by a leaflet with suspension members attached to a central support structure was lower than the stress on the leaflet when only suspension members were coupled to the stent (with no central support structure). The first design was an eight suspension member per leaflet design, with three suspension members attached to the leaflet free edge, one suspension member attached to each commissure region, and three suspension members attached to the belly region. All suspension members were attached to a substantially bell-shaped central support structure as described herein. The second design was a nine suspension member per leaflet design, with all suspension members being attached to the free edge of the leaflet. All suspension members were attached to a substantially bell-shaped central support structure as described herein. FIGS. 18A and 18B show the two designs with suspension members attached to a central support structure. The results of the comparison between two heart valves without central support structures and the same two heart valves with central support structures included are summarized in the following table:

| | Stress (psi) |
| --- | --- |
| 8-suspension members connected to stent | 93.15 |
| 8-suspension members connected to central support structure | 77.35 |
| 9-suspension members connected to stent | 88.97 |
| 9-suspension members connected to central support structure | 75.69 |

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A prosthetic heart valve for implantation into a selected channel within the heart of a subject, wherein blood flows through the selected channel in a flow direction, the prosthetic heart valve comprising:
   a stent having an inner surface, the inner surface of the stent defining an interior region of the stent, wherein the stent is radially collapsible and expandable to an expanded configuration;
   a lining skirt positioned within the interior space of the stent, wherein the lining skirt is radially collapsible and expandable with the stent;
   a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet;
   a suspension assembly comprising:
      a central support structure coupled to the stent such that the central support structure is spaced from the plurality of leaflets in the flow direction; and
      a plurality of elongate suspension members secured thereto the central support structure, at least one suspension member of the plurality of suspension members being secured thereto each respective leaflet,
   wherein, following implantation of the prosthetic heart valve within the selected channel, the suspension assembly is configured to mechanically reinforce the plurality of leaflets, wherein the attachment edge of each leaflet is attached to the stent through the lining skirt, and wherein the central support structure of the suspension assembly is coupled to the stent through the lining skirt.

2. The prosthetic heart valve of claim 1, wherein the plurality of leaflets and the suspension assembly are radially collapsible and expandable with the stent.

3. The prosthetic heart valve of claim 1, wherein the stent comprises a shape-memory material that is configured to expand the stent into the expanded configuration, wherein, in the expanded configuration, the inner surface of the stent defines a desired cross-sectional profile.

4. The prosthetic heart valve of claim 1, wherein at least one leaflet of the plurality of leaflets has a substantially different size than another leaflet of the plurality of leaflets.

5. The prosthetic heart valve of claim 1, wherein at least a portion of the central support structure is uniformly spaced from the inner surface of the stent and at least a portion of the central support structure is directly secured to the stent.

6. The prosthetic heart valve of claim 1, wherein at least a portion of the central support structure is coupled to the stent by at least one connecting member and at least a portion of the central support structure is directly secured to the stent.

7. The prosthetic heart valve of claim 1, wherein the central support structure comprises a plurality of offset support members spaced circumferentially about the inner surface of the valve such that each support member of the plurality of support members spans between two points on the inner surface of the valve and overlaps with at least one other support member at an intersection point.

8. The prosthetic heart valve of claim 7, wherein each suspension member of the plurality of suspension members is secured to the central support structure at an intersection point.

9. The prosthetic heart valve of claim 1, wherein the support assembly comprises at least one substructure that extends from the central support member to a point on the stent that is spaced from the central support structure in a direction opposite the flow direction.

10. The prosthetic heart valve of claim 1, wherein at least one suspension member of the plurality of suspension members is secured to each commissure region of at least one leaflet of the plurality of leaflets.

11. The prosthetic heart valve of claim 1, wherein at least one suspension member of the plurality of suspension members is secured to the free edge of at least one leaflet of the plurality of leaflets.

12. The prosthetic heart valve of claim 1, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

13. The prosthetic heart valve of claim 1, wherein, following implantation of the prosthetic heart valve within the selected channel of the heart of the subject, at least one suspension member of the plurality of elongate suspension members is configured to be angularly oriented relative to the free edge of the leaflet of the plurality of leaflets to which it is attached.

14. The prosthetic heart valve of claim 1, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

15. The prosthetic heart valve of claim 1, wherein the free edge of at least one leaflet of the plurality of leaflets comprises an extended edge portion that, following implantation of the prosthetic heart valve within the selected chamber of the heart of the subject, is configured to project from the leaflet in the flow direction, and wherein at least one suspension member of the plurality of suspension members is secured to the extended edge portion of the at least one leaflet of the plurality of leaflets.

16. The prosthetic heart valve of claim 1, wherein the plurality of suspension members are secured to the central support structure at a plurality of attachment points, and wherein the plurality of attachment points are substantially positioned within a common plane when the prosthetic heart valve is in an unloaded state.

17. A prosthetic heart valve for implantation into a selected channel within the heart of a subject, wherein blood flows through the selected channel in a flow direction, the prosthetic heart valve comprising:
   a stent having an inner surface, the inner surface of the stent defining an interior region of the stent;
   a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet; and
   a suspension assembly comprising:
      a central support structure coupled to the stent such that the central support structure is spaced from the plurality of leaflets in the flow direction; and
      a plurality of elongate suspension members secured thereto the central support structure, at least one suspension member of the plurality of suspension members being secured thereto each respective leaflet,
   wherein, following implantation of the prosthetic heart valve within the selected channel, the suspension assembly is configured to mechanically reinforce the plurality of leaflets, and wherein at least a portion of the central support structure is uniformly spaced from the inner surface of the stent and at least a portion of the central support structure is directly secured to the stent.

18. The prosthetic heart valve of claim 17, wherein the stent is radially collapsible and expandable to an expanded configuration.

19. The prosthetic heart valve of claim 18, wherein the plurality of leaflets and the suspension assembly are radially collapsible and expandable with the stent.

20. The prosthetic heart valve of claim 18, wherein the stent comprises a shape-memory material that is configured to expand the stent into the expanded configuration, wherein, in the expanded configuration, the inner surface of the stent defines a desired cross-sectional profile.

21. The prosthetic heart valve of claim 18, further comprising a lining skirt positioned within the interior space of the stent, wherein the attachment edge of each leaflet is attached to the stent through the lining skirt, wherein the central support structure of the suspension assembly is coupled to the stent through the lining skirt, and wherein the lining skirt is radially collapsible and expandable with the stent.

22. The prosthetic heart valve of claim 17, wherein at least one leaflet of the plurality of leaflets has a substantially different size than another leaflet of the plurality of leaflets.

23. The prosthetic heart valve of claim 17, wherein at least a portion of the central support structure is coupled to the stent by at least one connecting member and at least a portion of the central support structure is directly secured to the stent.

24. The prosthetic heart valve of claim 17, wherein the central support structure comprises a plurality of offset support members spaced circumferentially about the inner surface of the valve such that each support member of the plurality of support members spans between two points on the inner surface of the valve and overlaps with at least one other support member at an intersection point.

25. The prosthetic heart valve of claim 24, wherein each suspension member of the plurality of suspension members is secured to the central support structure at an intersection point.

26. The prosthetic heart valve of claim 17, wherein the support assembly comprises at least one sub-structure that extends from the central support member to a point on the stent that is spaced from the central support structure in a direction opposite the flow direction.

27. The prosthetic heart valve of claim 17, wherein at least one suspension member of the plurality of suspension members is secured to each commissure region of at least one leaflet of the plurality of leaflets.

28. The prosthetic heart valve of claim 17, wherein at least one suspension member of the plurality of suspension members is secured to the free edge of at least one leaflet of the plurality of leaflets.

29. The prosthetic heart valve of claim 17, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

30. The prosthetic heart valve of claim 17, wherein, following implantation of the prosthetic heart valve within the selected channel of the heart of the subject, at least one suspension member of the plurality of elongate suspension members is configured to be gularly oriented relative to the free edge of the leaflet of the plurality of leaflets to which it is attached.

31. The prosthetic heart valve of claim 17, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

32. The prosthetic heart valve of claim 17, wherein the free edge of at least one leaflet of the plurality of leaflets comprises an extended edge portion that, following implantation of the prosthetic heart valve within the selected chamber of the heart of the subject, is configured to project from the leaflet in the flow direction, and wherein at least one suspension member of the plurality of suspension members is secured to the extended edge portion of the at least one leaflet of the plurality of leaflets.

33. The prosthetic heart valve of claim 17, wherein the plurality of suspension members are secured to the central support structure at a plurality of attachment points, and wherein the plurality of attachment points are substantially positioned within a common plane when the prosthetic heart valve is in an unloaded state.

34. A prosthetic heart valve for implantation into a selected channel within the heart of a subject, wherein blood flows through the selected channel in a flow direction, the prosthetic heart valve comprising:
a stent having an inner surface, the inner surface of the stent defining an interior region of the stent;
a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet; and
a suspension assembly comprising:
a central support structure coupled to the stent such that the central support structure is spaced from the plurality of leaflets in the flow direction; and
a plurality of elongate suspension members secured thereto the central support structure, at least one suspension member of the plurality of suspension members being secured thereto each respective leaflet,
wherein, following implantation of the prosthetic heart valve within the selected channel, the suspension assembly is configured to mechanically reinforrce the plurality of leaflets, and wherein at least a portion of the central support structure is coupled to the stent by at least one connecting member and at least a portion of the central support structure is directly secured to the stent.

35. The prosthetic heart valve of claim 34, wherein the stent is radially collapsible and expandable to an expanded configuration.

36. The prosthetic heart valve of claim 35, wherein the plurality of leaflets and the suspension assembly are radially collapsible and expandable with the stent.

37. The prosthetic heart valve of claim 35, wherein the stent comprises a shape-memory material that is configured to expand the stent into the expanded configuration, wherein, in the expanded configuration, the inner surface of the stent defines a desired cross-sectional profile.

38. The prosthetic heart valve of claim 35, further comprising a lining skirt positioned within the interior space of the stent, wherein the attachment edge of each leaflet is attached to the stent through the lining skirt, wherein the central support structure of the suspension assembly is coupled to the stent through the lining skirt, and wherein, the lining skirt is radially collapsible and expandable with the stent.

39. The prosthetic heart valve of claim 34, wherein at least one leaflet of the plurality of leaflets has a substantially different size than another leaflet of the plurality of leaflets.

40. The prosthetic heart valve of claim 34, wherein at least a portion of the central support structure is uniformly spaced from the inner surface of the stent and at least a portion of the central support structure is directly secured to the stent.

41. The prosthetic heart valve of claim 34, wherein the central support structure comprises a plurality of offset support members spaced circumferentially about the inner surface of the valve such that each support member of the plurality of support members spans between two points on the inner surface of the valve and overlaps with at least one other support member at an intersection point.

42. The prosthetic heart valve of claim 41, wherein each suspension member of the plurality of suspension members is secured to the central support structure at an intersection point.

43. The prosthetic heart valve of claim 34, wherein the support assembly comprises at least one sub-structure that extends from the central support member to a point on the stent that is spaced from the central support structure in a direction opposite the flow direction.

44. The prosthetic heart valve of claim 34, wherein at least one suspension member of the plurality of suspension members is secured to each conunissure region of at least one leaflet of the plurality of leaflets.

45. The prosthetic heart valve of claim 34, wherein at least one suspension member of the plurality of suspension members is secured to the free edge of at least one leaflet of the plurality of leaflets.

46. The prosthetic heart valve of claim 34, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

47. The prosthetic heart valve of claim 34, wherein, following implantation of the prosthetic heart valve within the selected channel of the heart of the subject, at least one suspension member of the plurality of elongate suspension members is configured to be angularly oriented relative to the free edge of the leaflet of the plurality of leaflets to which it is attached.

48. The prosthetic heart valve of claim 34, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

49. The prosthetic heart valve of claim 34, wherein the free edge of at least one leaflet of the plurality of leaflets comprises an extended edge portion that, following implantation of the prosthetic heart valve within the selected chamber of the heart of the subject, is configured to project from the leaflet in the flow direction, and wherein at least one suspension member of the plurality of suspension members is secured to the extended edge portion of the at least one leaflet of the plurality of leaflets.

50. The prosthetic heart valve of claim 34, wherein the plurality of suspension members are secured to the central support structure at a plurality of attachment points, and wherein the plurality of attachment points are substantially positioned within, a common plane when the prosthetic heart valve is in an unloaded state.

51. A prosthetic heart valve for implantation into a selected channel within the heart of a subject, wherein blood flows through the selected channel in a flow direction, the prosthetic heart valve comprising:
  a stent having an inner surface, the inner surface of the stent defining an interior region of the stent;
  a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet; and
  a suspension assembly comprising:
    a central support structure coupled to the stent such that the central support structure is spaced from the plurality of leaflets in the flow direction; and
    a plurality of elongate suspension members secured thereto the central support structure, at least one suspension member of the plurality of suspension members being secured thereto each respective leaflet,
  wherein, following implantation of the prosthetic heart valve within the selected channel, the suspension assembly is configured to mechanically reinforce the plurality of leaflets, and wherein at least one suspension member of the plurality of suspension members is secured to each commissure region of at least one leaflet of the plurality of leaflets.

52. The prosthetic heart valve of claim 51, wherein the stent is radially collapsible and expandable to an expanded configuration.

53. The prosthetic heart valve of claim 52, wherein the plurality of leaflets and the suspension assembly are radially collapsible and expandable with the stent.

54. The prosthetic heart valve of claim 52, wherein the stent comprises a shape-memory material that is configured to expand the stent into the expanded configuration, wherein, in the expanded configuration, the inner surface of the stent defines a desired cross-sectional profile.

55. The prosthetic heart valve of claim 52, further comprising a lining skirt positioned within the interior space of the stent, wherein the attachment edge of each leaflet is attached to the stent through the lining skirt, wherein the central support structure of the suspension assembly is coupled to the stent through the lining skirt, and wherein the lining skirt is radially collapsible and expandable with the stent.

56. The prosthetic heart valve of claim 51, wherein at least one leaflet of the plurality of leaflets has a substantially different size than another leaflet of the plurality of leaflets.

57. The prosthetic heart valve of claim 51, wherein at least a portion of the central support structure is uniformly spaced from the inner surface of the stent and at least a portion of the central support structure is directly secured to the stent.

58. The prosthetic heart valve of claim 51, wherein at least a portion of the central support structure is coupled to the stent by at least one connecting member and at least a portion of the central support structure is directly secured to the stent.

59. The prosthetic heart valve of claim 51, wherein the central support structure comprises a plurality of offset support members spaced circumferentially about the inner surface of the valve such that each support member of the plurality of support members spans between two points on the inner surface of the valve and overlaps with at least one other support member at an intersection point.

60. The prosthetic heart valve of claim 59, wherein each suspension member of the plurality of suspension members is secured to the central support structure at an intersection point.

61. The prosthetic heart valve of claim 51, wherein the support assembly comprises at least one sub-structure that extends from the central support member to a point on the stent that is spaced from the central support structure in a direction opposite the flow direction.

62. The prosthetic heart valve of claim 51, wherein at least one suspension member of the plurality of suspension members is secured to the free edge of at least one leaflet of the plurality of leaflets.

63. The prosthetic heart valve of claim 51, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

64. The prosthetic heart valve of claim 51, wherein, following implantation of the prosthetic heart valve within the selected channel of the heart of the subject, at least one suspension member of the plurality of elongate suspension members is configured to be angularly oriented relative to the free edge of the leaflet of the plurality of leaflets to which it is attached.

65. The prosthetic heart valve of claim 51, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

66. The prosthetic heart valve of claim 51, wherein the free edge of at least one leaflet of the plurality of leaflets comprises an extended edge portion that, following implantation of the prosthetic heart valve within the selected chamber of the heart of the subject, is configured to project from the leaflet in the flow direction, and wherein at least one suspension member of the plurality of suspension members is secured to the extended edge portion of the at least one leaflet of the plurality of leaflets.

67. The prosthetic heart valve of claim 51, wherein the plurality of suspension members are secured to the central support structure at a plurality of attachment points, and wherein the plurality of attachment points are substantially positioned within a common plane when the prosthetic heart valve is in an unloaded state.

68. A prosthetic heart valve for implantation into a selected channel within the heart of a subject, wherein blood flows through the selected channel in a flow direction, the prosthetic heart valve comprising:
a stent having an inner surface, the inner surface of the stent defining an interior region of the stent;
a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet; and
a suspension assembly comprising:
a central support structure coupled to the stent such that the central support structure is spaced from the plurality of leaflets in the flow direction; and
a plurality of elongate suspension members secured thereto the central support structure, at least one suspension member of the plurality of suspension members being secured thereto each respective leaflet,
wherein, following implantation of the prosthetic heart valve within the selected channel, the suspension assembly is configured to mechanically reinforce the plurality of leaflets, and
wherein at least one suspension member of the plurality of suspension members is secured to the free edge of at least one leaflet of the plurality of leaflets.

69. The prosthetic heart valve of claim 68, wherein the stent is radially collapsible and expandable to an expanded configuration.

70. The prosthetic heart valve of claim 69, wherein the plurality of leaflets and the suspension assembly are radially collapsible and expandable with the stent.

71. The prosthetic heart valve of claim 69, wherein the stent comprises a shape-memory material that is configured to expand the stent into the expanded configuration, wherein, in the expanded configuration, the inner surface of the stent defines a desired cross-sectional profile.

72. The prosthetic heart valve of claim 69, further comprising a lining skirt positioned within the interior space of the stent, wherein the attachment edge of each leaflet is attached to the stent through the lining skirt, wherein the central support structure of the suspension assembly is coupled to the stent through the lining skirt, and wherein the lining skirt is radially collapsible and expandable with the stent.

73. The prosthetic heart valve of claim 68, wherein at least one leaflet of the plurality of leaflets has a substantially different size than another leaflet of the plurality of leaflets.

74. The prosthetic heart valve of claim 68, wherein at least a portion of the central support structure is uniformly spaced from the inner surface of the stent and at least a portion of the central support structure is directly secured to the stent.

75. The prosthetic heart valve of claim 68, wherein at least a portion of the central support structure is coupled to the stent by at least one connecting member and at least a portion of the central support structure is directly secured to the stent.

76. The prosthetic heart valve of claim 68, wherein the central support structure comprises a plurality of offset support members spaced circumferentially about the inner surface of the valve such that each support member of the plurality of support members spans between two points on the inner surface of the valve and overlaps with at least one other support member at an intersection point.

77. The prosthetic heart valve of claim 76, wherein each suspension member of the plurality of suspension members is secured to the central support structure at an intersection point.

78. The prosthetic heart valve of claim 68, wherein the support assembly comprises at least one sub-structure that extends from the central support member to a point on the stent that is spaced from the central support structure in a direction opposite the flow direction.

79. The prosthetic heart valve of claim 68, wherein at least one suspension member of the plurality of suspension members is secured to each commissure region of at least one leaflet of the plurality of leaflets.

80. The prosthetic heart valve of claim 68, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

81. The prosthetic heart valve of claim 68, wherein, following implantation of the prosthetic heart valve within the selected channel of the heart of the subject, at least one suspension member of the plurality of elongate suspension members is configured to be angularly oriented relative to the free edge of the leaflet of the plurality of leaflets to which it is attached.

82. The prosthetic heart valve of claim 68, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

83. The prosthetic heart valve of claim 68, wherein the free edge of at least one leaflet of the plurality of leaflets comprises an extended edge portion that, following implantation of the prosthetic heart valve within the selected chamber of the heart of the subject, is configured to project from the leaflet in the flow direction, and wherein at least one suspension member of the plurality of suspension members is secured to the extended edge portion of the at least one leaflet of the plurality of leaflets.

84. The prosthetic heart valve of claim 68, wherein the plurality of suspension members are secured to the central support structure at a plurality of attachment points, and wherein the plurality of attachment points are substantially positioned within a common plane when the prosthetic heart valve is in an unloaded state.

85. A prosthetic heart valve for implantation into a selected channel within the heart of a subject, wherein blood flows through the selected channel in a flow direction, the prosthetic heart valve comprising:
a stent having an inner surface, the inner surface of the stent defining an interior region of the stent;
a plurality of leaflets positioned within the interior region of the stent, each leaflet of the plurality of leaflets defining a free edge, an attachment edge, and a pair of spaced commissure regions, the attachment edge of each leaflet being attached to the stent such that each commissure region of each respective leaflet is positioned proximate a commissure region of an adjacent leaflet, wherein the free edge of at least one leaflet of the plurality of leaflets comprises an extended edge portion that, following implantation of the prosthetic heart valve within the selected chamber of the heart of the subject, is configured to project from the leaflet in the flow direction; and
a suspension assembly comprising:
   a central support structure coupled to the stent such that the central support structure is spaced from the plurality of leaflets in the flow direction; and
   a plurality of elongate suspension members secured thereto the central support structure, at least one suspension member of the plurality of suspension members being secured thereto each respective leaflet,
wherein, following implantation of the prosthetic heart valve within the selected channel, the suspension assembly is configured to mechanically reinforce the plurality of leaflets, and
wherein at least one suspension member of the plurality of suspension members is secured to the extended edge portion of the at least one leaflet of the plurality of leaflets.

86. The prosthetic heart valve of claim 85, wherein the stent is radially collapsible and expandable to an expanded configuration.

87. The prosthetic heart valve of claim 86, wherein the plurality of leaflets and the suspension assembly are radially collapsible and expandable with the stent.

88. The prosthetic heart valve of claim 86, wherein the stent comprises a shape-memory material that is configured to expand the stent into the expanded configuration, wherein, in the expanded configuration, the inner surface of the stent defines a desired cross-sectional profile.

89. The prosthetic heart valve of claim 86, further comprising a lining skirt positioned within the interior space of the stent, wherein the attachment edge of each leaflet is attached to the stent through the lining skirt, wherein the central support structure of the suspension assembly is coupled to the stent through the lining skirt, and wherein the lining skirt is radially collapsible and expandable with the stent.

90. The prosthetic heart valve of claim 85, wherein at least one leaflet of the plurality of leaflets has a substantially different size than another leaflet of the plurality of leaflets.

91. The prosthetic heart valve of claim 85, wherein at least a portion of the central support structure is uniformly spaced from the inner surface of the stent and at least a portion of the central support structure is directly secured to the stent.

92. The prosthetic heart valve of claim 85, wherein at least a portion of the central support structure is coupled to the stent by at least one connecting member and at least a portion of the central support structure is directly secured to the stent.

93. The prosthetic heart valve of claim 85, wherein the central support structure comprises a plurality of offset support members spaced circumferentially about the inner surface of the valve such that each support member of the plurality of support members spans between two points on the inner surface of the valve and overlaps with at least one other support member at an intersection point.

94. The prosthetic heart valve of claim 93, wherein each suspension member of the plurality of suspension members is secured to the central support structure at an intersection point.

95. The prosthetic heart valve of claim 85, wherein the support assembly comprises at least one sub-structure that extends from the central support member to a point on the stent that is spaced from the central support structure in a direction opposite the flow direction.

96. The prosthetic heart valve of claim 85, wherein at least one suspension member of the plurality of suspension members is secured to each commissure region of at least one leaflet of the plurality of leaflets.

97. The prosthetic heart valve of claim 85, wherein at least one suspension member of the plurality of suspension members is secured to the free edge of at least one leaflet of the plurality of leaflets.

98. The prosthetic heart valve of claim 85, wherein each leaflet of the plurality of leaflets defines a belly region positioned therebetween the free edge, the attachment edge, and the commissure regions of the leaflet, and wherein at least one suspension member of the plurality of suspension members is secured to the belly region of at least one leaflet.

99. The prosthetic heart valve of claim 85, wherein, following implantation of the prosthetic heart valve within the selected channel of the heart of the subject, at least one suspension member of the plurality of elongate suspension members is configured to be angularly oriented relative to the free edge of the leaflet of the plurality of leaflets to which it is attached.

100. The prosthetic heart valve of claim 85, wherein, following implantation of the prosthetic heart valve within the selected channel of the heart of the subject, at least one suspension member of the plurality of elongate suspension members is configured to be substantially perpendicularly oriented relative to the free edge of the leaflet of the plurality of leaflets to which it is attached.

101. The prosthetic heart valve of claim 85, wherein the plurality of suspension members are secured to the central support structure at a plurality of attachment points, and wherein the plurality of attachment points are substantially positioned within a common plane when the prosthetic heart valve is in an unloaded state.

* * * * *